United States Patent
Collins et al.

(10) Patent No.: US 9,028,486 B2
(45) Date of Patent: May 12, 2015

(54) METHODS OF USING A CATHETER HAVING A BRAIDED CONDUCTIVE MEMBER

(75) Inventors: Russell F. Collins, Sandown, NH (US); Gary S. Falwell, Moultonborough, MA (US); Eric A. Bene, Lynn, MA (US); Steven J. Burns, Haverhill, MA (US); Denyse M. Collins, Derry, NH (US); Charles A. Gibson, Malden, MA (US); Ding Sheng He, Tyngsboro, MA (US); Paul E. LeClair, Merrimack, NH (US); Donald F. Patterson, North Chelmsford, MA (US); Stephen W. Sagon, Amherst, NH (US); Pierre Jais, St. Medard (FR)

(73) Assignee: Boston Scientific Scimed Inc., Maple Grove, MN (US)

( * ) Notice: Subject to any disclaimer, the term of this patent is extended or adjusted under 35 U.S.C. 154(b) by 297 days.

(21) Appl. No.: 13/414,018

(22) Filed: Mar. 7, 2012

(65) Prior Publication Data
US 2012/0165815 A1 Jun. 28, 2012

Related U.S. Application Data

(60) Continuation of application No. 11/978,066, filed on Oct. 26, 2007, now Pat. No. 8,157,796, which is a division of application No. 10/939,630, filed on Sep. 13, 2004, now Pat. No. 7,306,594, which is a division of application No. 09/845,022, filed on Apr. 27, 2001, now Pat. No. 6,837,886.

(60) Provisional application No. 60/201,445, filed on May 3, 2000, provisional application No. 60/204,457, filed on May 16, 2000, provisional application No. 60/204,482, filed on May 16, 2000, provisional application No. 60/261,015, filed on Jan. 11, 2001.

(51) Int. Cl.
*A61B 18/14* (2006.01)
*A61B 17/00* (2006.01)
*A61B 18/00* (2006.01)

(52) U.S. Cl.
CPC ....... *A61B 18/1492* (2013.01); *A61B 2017/003* (2013.01); *A61B 2018/00029* (2013.01); *A61B 2018/00083* (2013.01); *A61B 2018/0016* (2013.01); *A61B 2018/00196* (2013.01); *A61B 2018/00214* (2013.01); *A61B 2018/00267* (2013.01); *A61B 2018/00577* (2013.01); *A61B 2018/00797* (2013.01); *A61B 2018/00821* (2013.01); *A61B 2018/00946* (2013.01); *A61B 2018/1497* (2013.01)

(58) Field of Classification Search
USPC .......................................... 606/41–45, 48–50
See application file for complete search history.

(56) References Cited

U.S. PATENT DOCUMENTS 3,996,938 A 12/1976 Clark, III
4,660,571 A 4/1987 Hess et al.
(Continued)

FOREIGN PATENT DOCUMENTS

EP 0 428 279 4/1991
EP 0 771 547 A2 7/1997
(Continued)

*Primary Examiner* — Michael Peffley
(74) *Attorney, Agent, or Firm* — Seager, Tufte & Wickhem, LLC

(57) ABSTRACT

Embodiments described herein relate to methods of using a catheter having a braided conductive member. One embodiment relates to a method for treating a condition of a patient that involves contacting an exterior wall of a blood vessel with the braided conductive member. Another embodiment relates to a method that involves contacting a wall of a blood vessel with the braided conductive member and controlling energy delivery to the braided conductive member based on at least one sensed temperature.

12 Claims, 22 Drawing Sheets

(56) References Cited

U.S. PATENT DOCUMENTS

| | | |
|---|---|---|
| 4,664,120 A | 5/1987 | Hess |
| 4,699,147 A | 10/1987 | Chilson et al. |
| 4,709,698 A | 12/1987 | Johnston et al. |
| 4,921,404 A | 5/1990 | Holmberg |
| 4,921,484 A | 5/1990 | Hillstead |
| 4,940,064 A | 7/1990 | Desai |
| 4,998,539 A | 3/1991 | Delsanti |
| 5,010,894 A | 4/1991 | Edhag |
| 5,100,423 A | 3/1992 | Fearnot |
| 5,190,542 A | 3/1993 | Nakao et al. |
| 5,215,103 A | 6/1993 | Desai |
| 5,231,995 A | 8/1993 | Desai |
| 5,255,679 A | 10/1993 | Imran |
| 5,311,866 A | 5/1994 | Kagan et al. |
| 5,313,943 A | 5/1994 | Houser et al. |
| 5,324,284 A | 6/1994 | Imran |
| 5,365,926 A | 11/1994 | Desai |
| 5,383,852 A | 1/1995 | Stevens-Wright et al. |
| 5,397,339 A | 3/1995 | Desai |
| 5,397,341 A | 3/1995 | Hirschberg et al. |
| 5,400,783 A | 3/1995 | Pomeranz et al. |
| 5,403,311 A | 4/1995 | Abele et al. |
| 5,409,000 A | 4/1995 | Imran |
| 5,415,166 A | 5/1995 | Imran |
| 5,433,198 A | 7/1995 | Desai |
| 5,465,717 A | 11/1995 | Imran et al. |
| 5,476,495 A | 12/1995 | Kordis et al. |
| 5,549,108 A | 8/1996 | Edwards et al. |
| 5,575,810 A | 11/1996 | Swanson et al. |
| 5,611,777 A | 3/1997 | Bowden et al. |
| 5,636,634 A | 6/1997 | Kordis et al. |
| 5,643,197 A * | 7/1997 | Brucker et al. .................. 604/20 |
| 5,653,684 A * | 8/1997 | Laptewicz et al. .............. 604/22 |
| 5,680,860 A | 10/1997 | Imran |
| 5,681,280 A | 10/1997 | Bowe et al. |
| 5,702,438 A | 12/1997 | Avitall |
| 5,722,403 A | 3/1998 | McGee et al. |
| 5,725,552 A | 3/1998 | Kotula et al. |
| 5,730,128 A | 3/1998 | Pomeranz et al. |
| 5,738,683 A | 4/1998 | Osypka |
| 5,800,482 A | 9/1998 | Pomeranz et al. |
| 5,813,997 A | 9/1998 | Quiachon et al. |
| 5,836,947 A | 11/1998 | Fleischman et al. |
| 5,860,974 A | 1/1999 | Abele |
| 5,868,706 A | 2/1999 | Cox |
| 5,879,348 A | 3/1999 | Owens et al. |
| 5,891,136 A | 4/1999 | McGee et al. |
| 5,893,885 A | 4/1999 | Webster, Jr. |
| 5,904,698 A | 5/1999 | Thomas et al. |
| 5,916,213 A | 6/1999 | Haissaguerre et al. |
| 5,921,982 A | 7/1999 | Lesh et al. |
| 5,928,260 A | 7/1999 | Chin et al. |
| 5,931,863 A | 8/1999 | Griffin, III et al. |
| 5,951,471 A | 9/1999 | de la Rama et al. |
| 5,968,040 A | 10/1999 | Swanson et al. |
| 5,997,536 A | 12/1999 | Osswald et al. |
| 6,001,093 A | 12/1999 | Swanson et al. |
| 6,012,457 A * | 1/2000 | Lesh ............................ 128/898 |
| 6,014,590 A | 1/2000 | Whayne et al. |
| 6,023,638 A | 2/2000 | Swanson |
| 6,029,671 A | 2/2000 | Stevens et al. |
| 6,052,607 A | 4/2000 | Edwards et al. |
| 6,071,282 A | 6/2000 | Fleischman |
| 6,119,030 A | 9/2000 | Morency |
| 6,142,993 A | 11/2000 | Whayne et al. |
| 6,146,379 A | 11/2000 | Fleischman et al. |
| 6,163,716 A | 12/2000 | Edwards et al. |
| 6,237,605 B1 * | 5/2001 | Vaska et al. .................. 128/898 |
| 6,240,307 B1 | 5/2001 | Beatty et al. |
| 6,315,778 B1 * | 11/2001 | Gambale et al. ................ 606/41 |
| 6,375,668 B1 | 4/2002 | Gifford et al. |
| 6,468,272 B1 | 10/2002 | Koblish et al. |
| 6,480,746 B1 | 11/2002 | Ingle et al. |
| 6,500,174 B1 | 12/2002 | Maguire et al. |
| 6,529,779 B1 | 3/2003 | Sutton |
| 6,572,609 B1 | 6/2003 | Farr et al. |
| 6,613,046 B1 * | 9/2003 | Jenkins et al. .................. 606/41 |
| 6,616,655 B1 * | 9/2003 | Falwell et al. .................. 606/41 |
| 6,647,617 B1 | 11/2003 | Beatty et al. |
| 6,673,290 B1 | 1/2004 | Whayne et al. |
| 6,702,811 B2 | 3/2004 | Stewart et al. |
| 6,786,905 B2 | 9/2004 | Swanson et al. |
| 6,837,886 B2 | 1/2005 | Collins et al. |
| 6,917,834 B2 | 7/2005 | Koblish et al. |
| 7,255,695 B2 | 8/2007 | Falwell et al. |
| 7,306,594 B2 * | 12/2007 | Collins et al. .................. 606/41 |
| 7,722,604 B2 | 5/2010 | Brown, III et al. |
| 7,727,229 B2 | 6/2010 | He et al. |
| 2001/0007070 A1 | 7/2001 | Stewart et al. |
| 2002/0107511 A1 | 8/2002 | Collins et al. |
| 2002/0169473 A1 | 11/2002 | Sepetka et al. |
| 2002/0188289 A1 | 12/2002 | Hegde |
| 2003/0078574 A1 | 4/2003 | Hall et al. |
| 2003/0093069 A1 | 5/2003 | Panescu et al. |
| 2003/0114739 A1 | 6/2003 | Fuimaono et al. |
| 2004/0044277 A1 | 3/2004 | Fuimaono et al. |
| 2004/0187875 A1 | 9/2004 | He et al. |
| 2008/0262337 A1 | 10/2008 | Falwell et al. |

FOREIGN PATENT DOCUMENTS

| | | |
|---|---|---|
| EP | 0 790 066 A2 | 8/1997 |
| EP | 0 982 047 A2 | 3/2000 |
| GB | 2271932 A | 4/1994 |
| JP | 54-150888 | 11/1979 |
| JP | 05-505118 | 8/1993 |
| JP | 11-500037 | 1/1999 |
| JP | 2000-508561 | 7/2000 |
| JP | 2001-509415 | 7/2001 |
| JP | 2002-508989 | 3/2002 |
| JP | 2003-513742 | 4/2003 |
| JP | 2003-514612 | 4/2003 |
| WO | WO 93/16632 A1 | 9/1993 |
| WO | WO 94/00178 A | 1/1994 |
| WO | WO 94/06349 A1 | 3/1994 |
| WO | WO 94/16618 | 8/1994 |
| WO | WO 94/21165 A1 | 9/1994 |
| WO | WO 94/21167 A1 | 9/1994 |
| WO | WO 94/21168 A1 | 9/1994 |
| WO | WO 95/01751 A1 | 1/1995 |
| WO | WO 95/10319 A1 | 4/1995 |
| WO | WO 96/25097 | 8/1996 |
| WO | WO 97/17892 A1 | 5/1997 |
| WO | WO 99/15225 A | 4/1999 |
| WO | WO 99/56812 A2 | 11/1999 |
| WO | WO 99/62413 A1 | 12/1999 |
| WO | WO 00/67656 A1 | 11/2000 |
| WO | WO 00/72909 A1 | 12/2000 |
| WO | WO 00/74555 | 12/2000 |
| WO | WO 01/17451 A1 | 3/2001 |
| WO | WO 01/82814 A2 | 11/2001 |
| WO | WO 01/95820 A | 12/2001 |
| WO | WO 02/087437 A | 11/2002 |
| WO | WO 02/087456 A | 11/2002 |
| WO | WO 02/087679 A2 | 11/2002 |
| WO | WO 05/112813 A1 | 12/2005 |

* cited by examiner

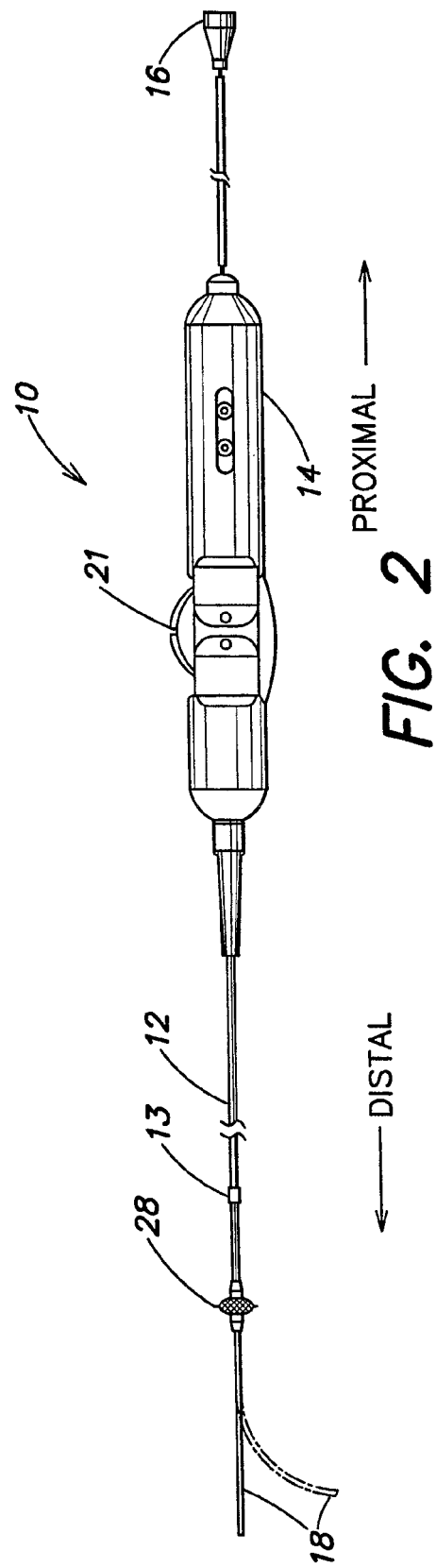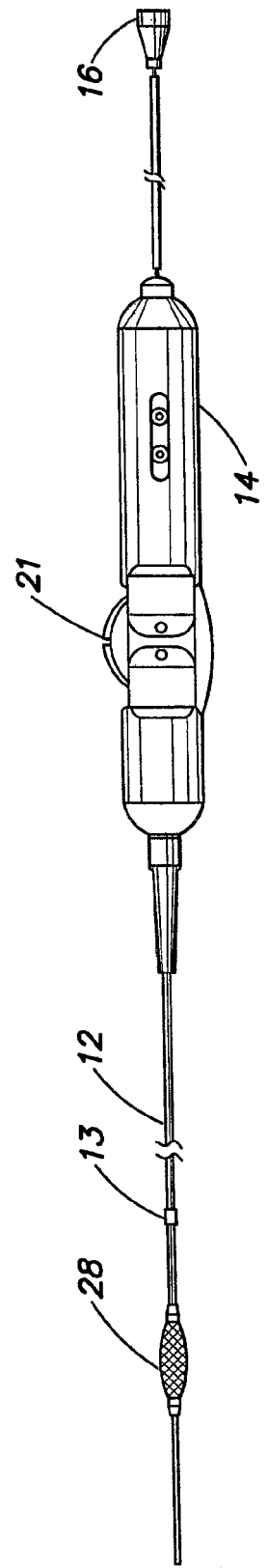
FIG. 2
FIG. 3

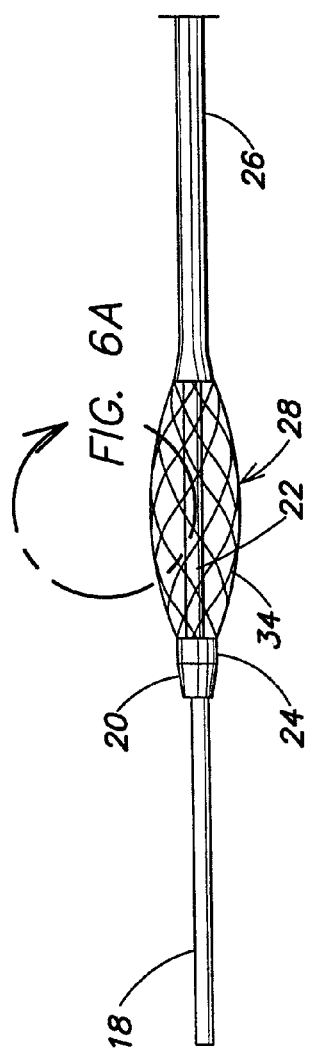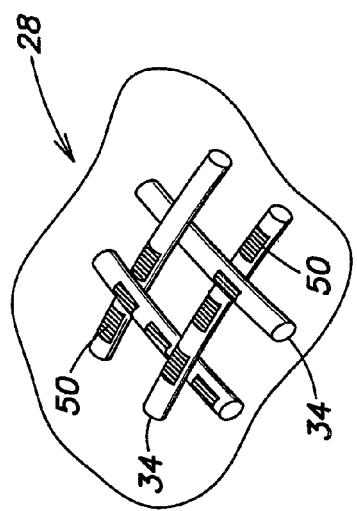

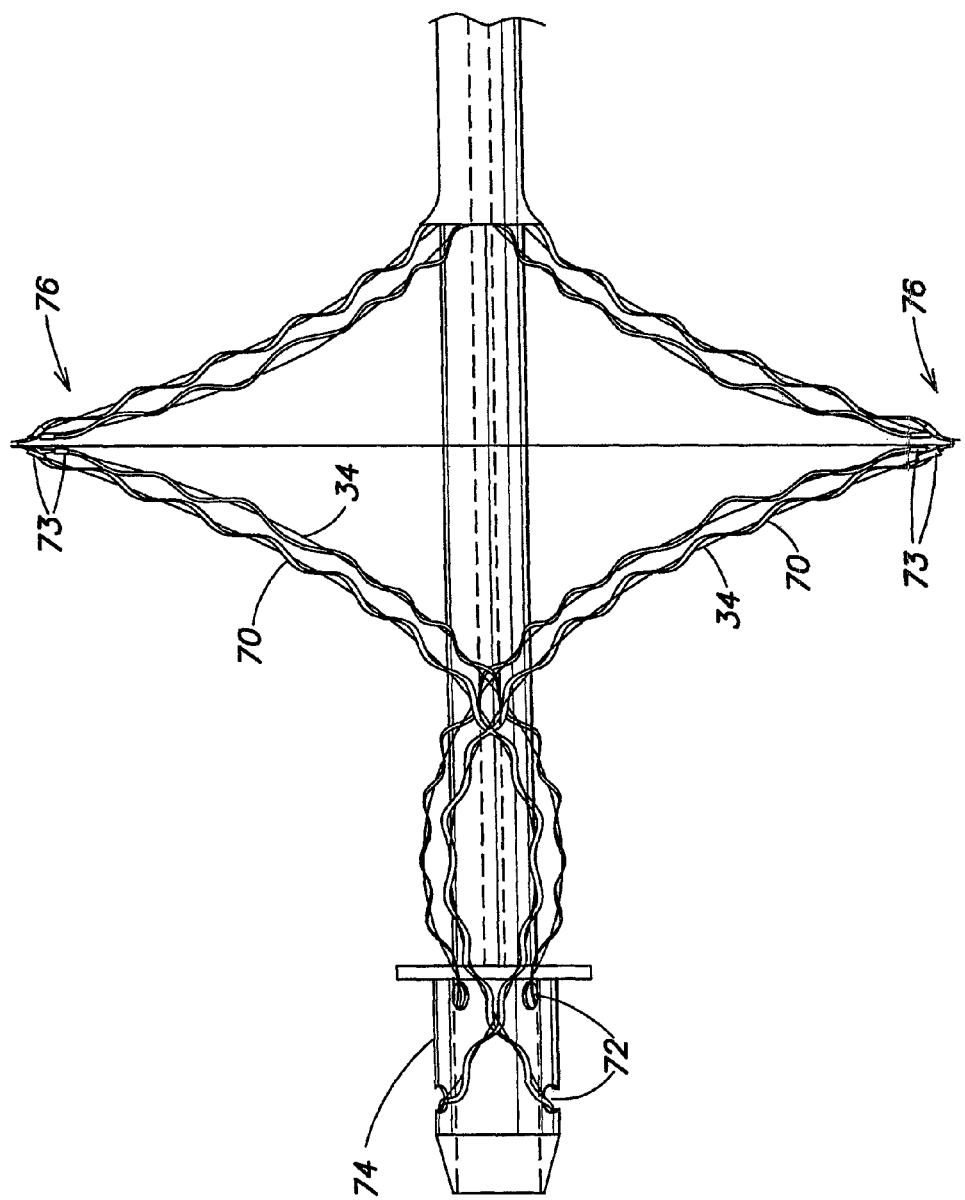

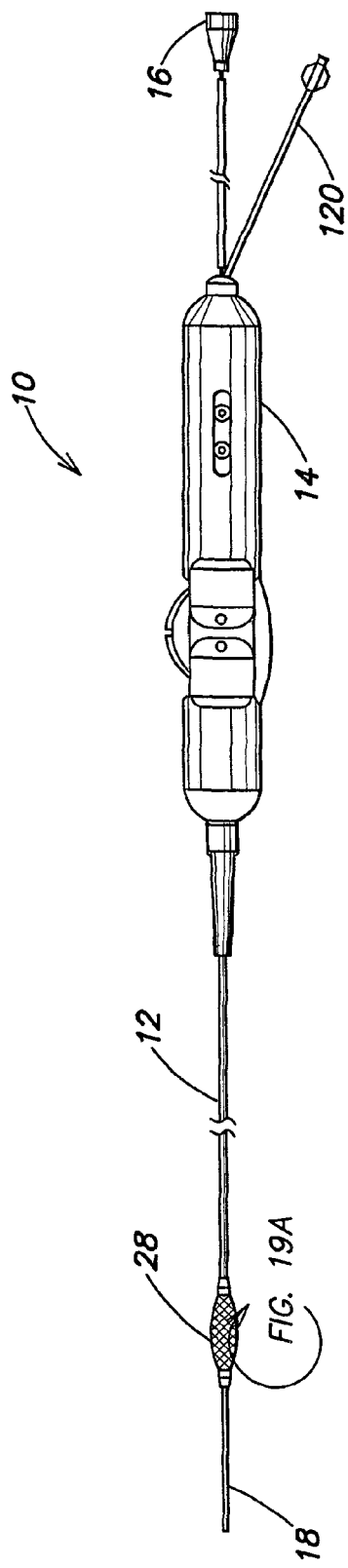
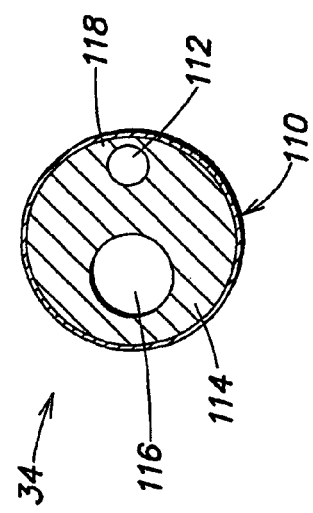
FIG. 19
FIG. 19A

METHODS OF USING A CATHETER HAVING A BRAIDED CONDUCTIVE MEMBER

CROSS REFERENCE TO RELATED APPLICATIONS

The present application is a continuation of U.S. application Ser. No. 11/978,066, filed Oct. 26, 2007, now U.S. Pat. No. 8,157,796; which is a divisional of U.S. application Ser. No. 10/939,630, filed Sep. 13, 2004, now U.S. Pat. No. 7,306,594; which is a divisional of U.S. application Ser. No. 09/845,022, filed Apr. 27, 2001, now U.S. Pat. No. 6,837,886; all of which are entitled APPARATUS AND METHODS FOR MAPPING AND ABLATION IN ELECTROPHYSIOLOGY PROCEDURES, all of which are hereby incorporated herein by reference in their entirety, and which, in turn, claim the benefit of U.S. Provisional Application Ser. No. 60/261,015 entitled HIGH DENSITY MAPPING AND ABLATION CATHETER AND METHOD OF USE, filed Jan. 11, 2001; U.S. Provisional Application Ser. No. 60/204,457 entitled METHOD FOR CREATING ANNULAR EPICARDIAL LESIONS AT THE OSTIA OF THE PULMONARY VEINS, filed on May 16, 2000; U.S. Provisional Application Ser. No. 60/204,482 entitled METHOD AND DEVICE FOR CREATING ANNULAR ENDOCARDIAL LESIONS AT THE OSTIA OF THE PULMONARY VEINS, filed May 16, 2000; and U.S. Provisional Application Ser. No. 60/201,445 entitled TRANSMURAL CIRCUMFERENTIAL LESIONS MADE AT CANINE PV OSTIUM BY EXPANDABLE MESH ELECTRODES IN VIVO, filed May 3, 2000, all of which are also hereby incorporated herein by reference in their entirety.

BACKGROUND OF THE INVENTION

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

Over time, the electrical impulses traveling through the heart can begin to travel in improper directions, thereby causing the heart chambers to contract at improper times. Such a condition is generally termed a cardiac arrhythmia, and can take many different forms. When the chambers contract at improper times, the amount of blood pumped by the heart decreases, which can result in premature death of the person.

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multichannel recorder at each of several different endocardial positions. When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

Atrial fibrillation together with atrial flutter are the most common sustained arrhythmias found in clinical practice.

Current understanding is that atrial fibrillation is frequently initiated by a focal trigger from the orifice of or within one of the pulmonary veins. Though mapping and ablation of these triggers appears to be curative in patients with paroxysmal atrial fibrillation, there are a number of limitations to ablating focal triggers via mapping and ablating the earliest site of activation with a "point" radiofrequency lesion. One way to circumvent these limitations is to determine precisely the point of earliest activation. Once the point of earliest activation is identified, a lesion can be generated to electrically isolate the trigger with a lesion; firing from within those veins would then be eliminated or unable to reach the body of the atrium, and thus could not trigger atrial fibrillation.

Another method to treat focal arrhythmias is to create a continuous, annular lesion around the ostia (i.e., the openings) of either the veins or the arteries leading to or from the atria thus "corralling" the signals emanating from any points distal to the annular lesion. Conventional techniques include applying multiple point sources around the ostia in an effort to create such a continuous lesion. Such a technique is relatively involved, and requires significant skill and attention from the clinician performing the procedures.

Another source of arrhythmias may be from reentrant circuits in the myocardium itself. Such circuits may not necessarily be associated with vessel ostia, but may be interrupted by means of ablating tissue either within the circuit or circumscribing the region of the circuit. It should be noted that a complete 'fence' around a circuit or tissue region is not always required in order to block the propagation of the arrhythmia; in many cases simply increasing the propagation path length for a signal may be sufficient. Conventional means for establishing such lesion 'fences' include a multiplicity of point-by-point lesions, dragging a single electrode across tissue while delivering energy, or creating an enormous lesion intended to inactivate a substantive volume of myocardial tissue.

Commonly-owned U.S. patent application Ser. No. 09/396,502, entitled Apparatus For Creating A Continuous Annular Lesion, which is hereby incorporated by reference, discloses a medical device which is capable of ablating a continuous ring of tissue around the ostia of either veins or arteries leading to or from the atria.

SUMMARY OF THE INVENTION

The present invention encompasses apparatus and methods for mapping electrical activity within the heart. The present invention also encompasses methods and apparatus for creating lesions in the heart tissue (ablating) to create a region of necrotic tissue which serves to disable the propagation of errant electrical impulses caused by an arrhythmia.

In one embodiment, the present invention includes a medical device including a catheter having a braided conductive member at a distal end thereof, a mechanism for expanding the braided conductive member from an undeployed to a deployed position, and a mechanism for applying energy via the braided conductive member to blood vessel.

In one embodiment, the medical device further includes a mechanism for irrigating the braided conductive member.

In another embodiment, the medical device further includes at least one reference electrode disposed on a shaft of the catheter.

In another embodiment, the medical device includes a mechanism for controlling the energy supplied to the braided conductive member.

In another embodiment, the medical device further includes a mechanism for covering at least a portion of the braided conductive member when the braided conductive member is in the deployed position.

In another embodiment, at least a portion of the braided conductive member has a coating applied thereto.

In another embodiment, the medical device includes a mechanism for measuring temperature.

In another embodiment, the medical device includes a mechanism for steering the catheter.

The invention also includes a method for treating cardiac arrhythmia, including the steps of introducing a catheter having a braided conductive member at a distal end thereof into a blood vessel, expanding the braided conductive member at a selected location in the blood vessel so that the braided conductive member contacts a wall of the blood vessel, and applying energy to the wall of the blood vessel via the braided conductive member to create a lesion in the blood vessel.

In another embodiment, the invention includes a method for treating cardiac arrhythmia, including the steps of introducing a catheter into a thoracic cavity of a patient, the catheter having a braided conductive member at a distal end thereof, contacting an exterior wall of a blood vessel in a vicinity of an ostium with the braided conductive member, and applying energy to the blood vessel via the braided conductive member to create a lesion on the exterior wall of the blood vessel.

Another embodiment described herein relates to a method for treating a condition of a patient. The method comprises acts of introducing a portion of a catheter into a patient, the catheter having a braided conductive member at a distal end thereof, contacting an exterior wall of a blood vessel with the braided conductive member, and applying energy to the exterior wall via the braided conductive member to treat the condition.

A further embodiment described herein relates to a method comprising an act of introducing a portion of a catheter into a patient, the catheter having a braided conductive member at a distal end thereof. The braided conductive member comprises a plurality of filaments. The method also comprises acts of contacting a wall of a blood vessel with the braided conductive member and energizing at least some of the plurality of filaments to apply energy to the wall via the braided conductive member. The method further comprises acts of sensing, during the act of energizing, at least one temperature using at least one temperature sensor coupled to the braided conductive member; and controlling energy delivery to the braided conductive member based on the at least one sensed temperature.

The braided conductive member may be a wire mesh.

The features and advantages of the present invention will be more readily understood and apparent from the following detailed description of the invention, which should be read in conjunction with the accompanying drawings, and from the claims which are appended at the end of the Detailed Description.

BRIEF DESCRIPTION OF THE DRAWINGS

In the drawings, which are incorporated herein by reference and in which like elements have been given like references characters.

FIGS. 2 and 3 illustrate further details of the catheter illustrated in FIG. 1;

FIGS. 4-7 illustrate further details of the braided conductive member illustrated in FIGS. 2 and 3;

FIGS. 8-10A illustrate, among other things, temperature sensing in the present invention;

FIGS. 18-19A illustrate the use of irrigation in connection with the present invention;

DETAILED DESCRIPTION

System Overview

Figure 1:
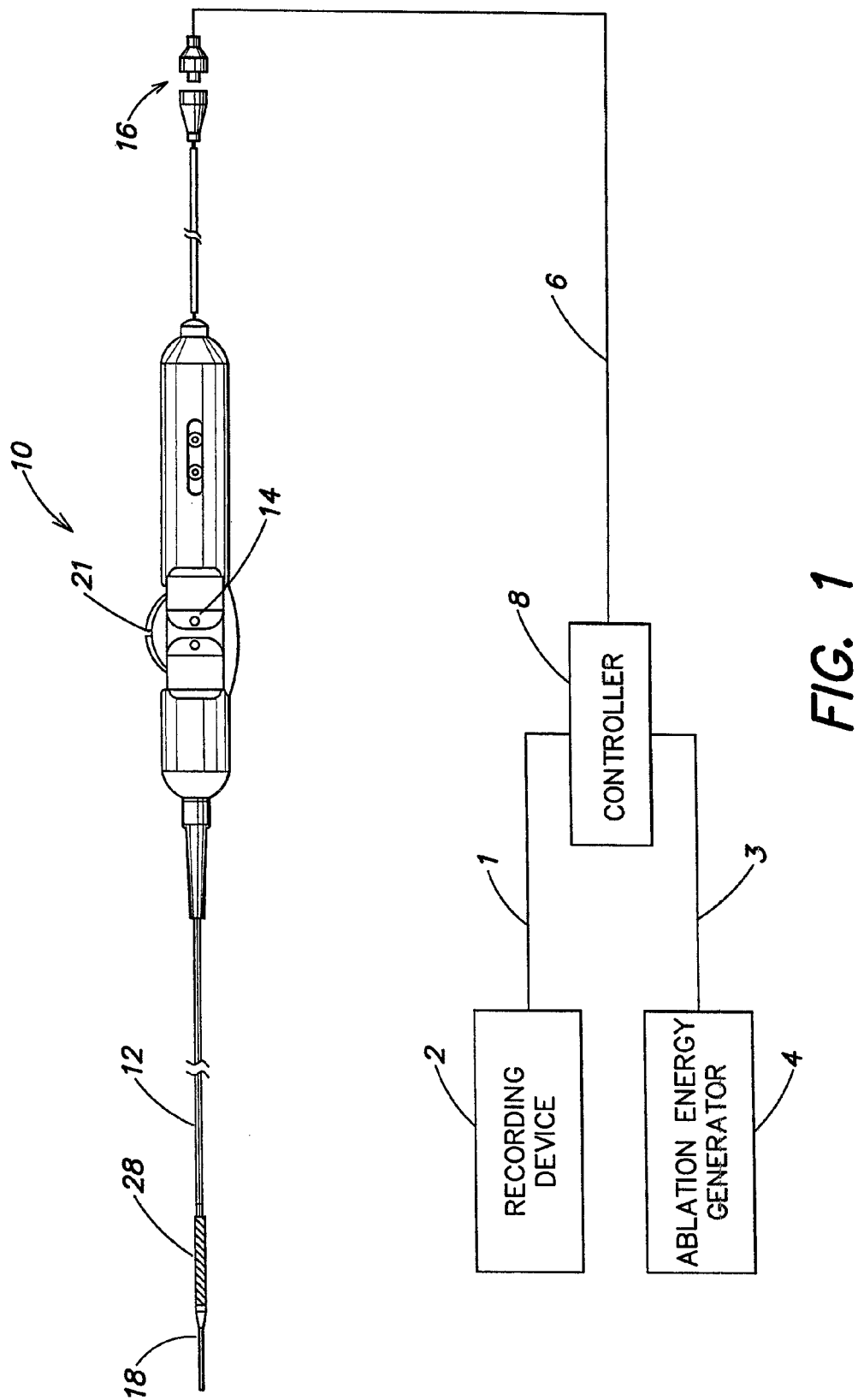
FIG. 1 illustrates an overview of a mapping and ablation catheter system in accordance with the present invention.

Reference is now made to FIG. 1, which figure illustrates an overview of a mapping and ablation catheter system in accordance with the present invention. The system includes a catheter 10 having a shaft portion 12, a control handle 14, and a connector portion 16. A controller 8 is connected to connector portion 16 via cable 6. Ablation energy generator 4 may be connected to controller 8 via cable 3. A recording device 2 may be connected to controller 8 via cable 1. When used in an ablation application, controller 8 is used to control ablation energy provided by ablation energy generator 4 to catheter 10. When used in a mapping application, controller 8 is used to process signals coming from catheter 10 and to provide these signals to recording device 2. Although illustrated as separate devices, recording device 2, ablation energy generator 4, and controller 8 could be incorporated into a single device. In one embodiment, controller 8 may be a QUADRAPULSE RF CONTROLLER™ device available from CR Bard, Inc., Murray Hill, N.J.

In this description, various aspects and features of the present invention will be described. The various features of the invention are discussed separately for clarity. One skilled in the art will appreciate that the features may be selectively combined in a device depending upon the particular application. Furthermore, any of the various features may be incorporated in a catheter and associated method of use for either mapping or ablation procedures.

Catheter Overview

Reference is now made to FIGS. 2-7, which figures illustrate one embodiment of the present invention. The present invention generally includes a catheter and method of its use for mapping and ablation in electrophysiology procedures. Catheter 10 includes a shaft portion 12, a control handle 14, and a connector portion 16. When used in mapping applications, connector portion 16 is used to allow signal wires running from the electrodes at the distal portion of the catheter to be connected to a device for processing the electrical signals, such as a recording device.

Catheter 10 may be a steerable device. FIG. 2 illustrates the distal tip portion 18 being deflected by the mechanism contained within control handle 14. Control handle 14 may include a rotatable thumb wheel which can be used by a user to deflect the distal end of the catheter. The thumb wheel (or any other suitable actuating device) is connected to one or more pull wires which extend through shaft portion 12 and are connected to the distal end 18 of the catheter at an off-axis location, whereby tension applied to one or more of the pull wires causes the distal portion of the catheter to curve in a predetermined direction or directions. U.S. Pat. Nos. 5,383,852, 5,462,527, and 5,611,777, which are hereby incorporated by reference, illustrate various embodiments of control handle 14 that may be used for steering catheter 10.

Shaft portion 12 includes a distal tip portion 18, a first stop 20 and an inner member 22 connected to the first stop portion 20. Inner member 22 may be a tubular member. Concentrically disposed about inner member 22 is a first sheath 24 and a second sheath 26. Also concentrically disposed about inner member 22 is a braided conductive member 28 anchored at respective ends 30 and 32 to the first sheath 24 and the second sheath 26, respectively.

Figure 4:
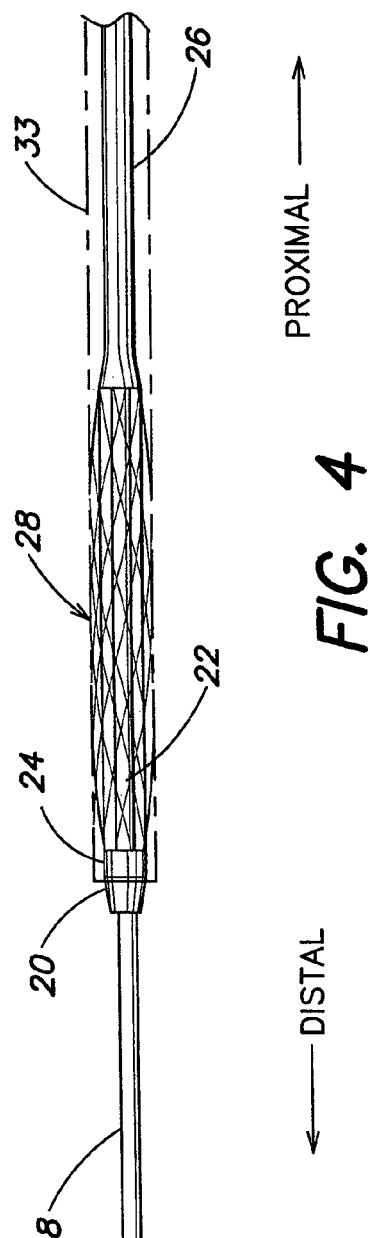

In operation, advancing the second sheath 26 distally over inner member 22 causes the first sheath 24 to contact stop 20. Further distal advancement of the second sheath 26 over inner member 22 causes the braided conductive member 28 to expand radially to assume various diameters and/or a conical shape. FIG. 3 illustrates braided conductive member 28 in an unexpanded (collapsed or "undeployed") configuration. FIGS. 2 and 4 illustrate braided conductive member 28 in a partially expanded condition. FIG. 1 illustrates braided conductive member 28 radially expanded ("deployed") to form a disk.

Alternatively, braided conductive member 28 can be radially expanded by moving inner member 22 proximally with respect to the second sheath 26.

As another alternative, inner member 22 and distal tip portion 18 may be the same shaft and stop 20 may be removed. In this configuration, sheath 24 moves over the shaft in response to, for example, a mandrel inside shaft 22 and attached to sheath 24 in the manner described, for example, in U.S. Pat. No. 6,178,354, which is incorporated herein by reference.

Figure 5:
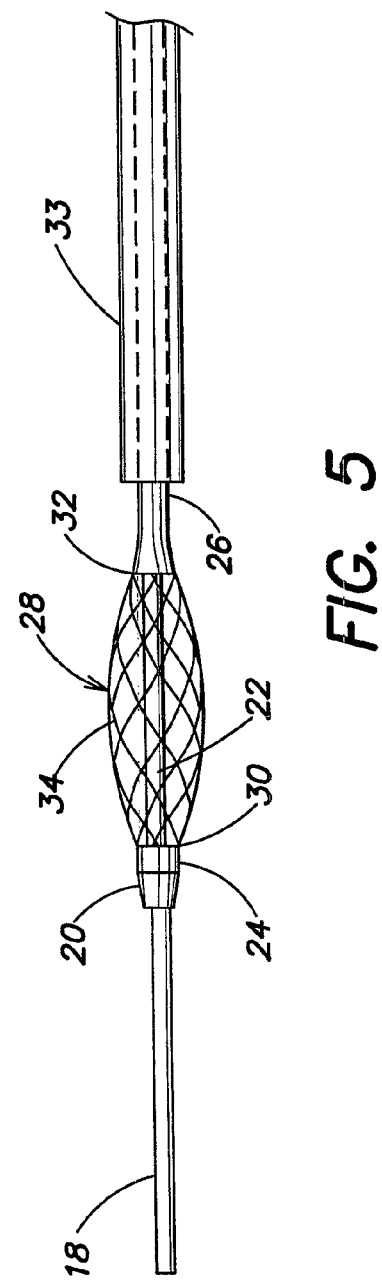
Figure 7:
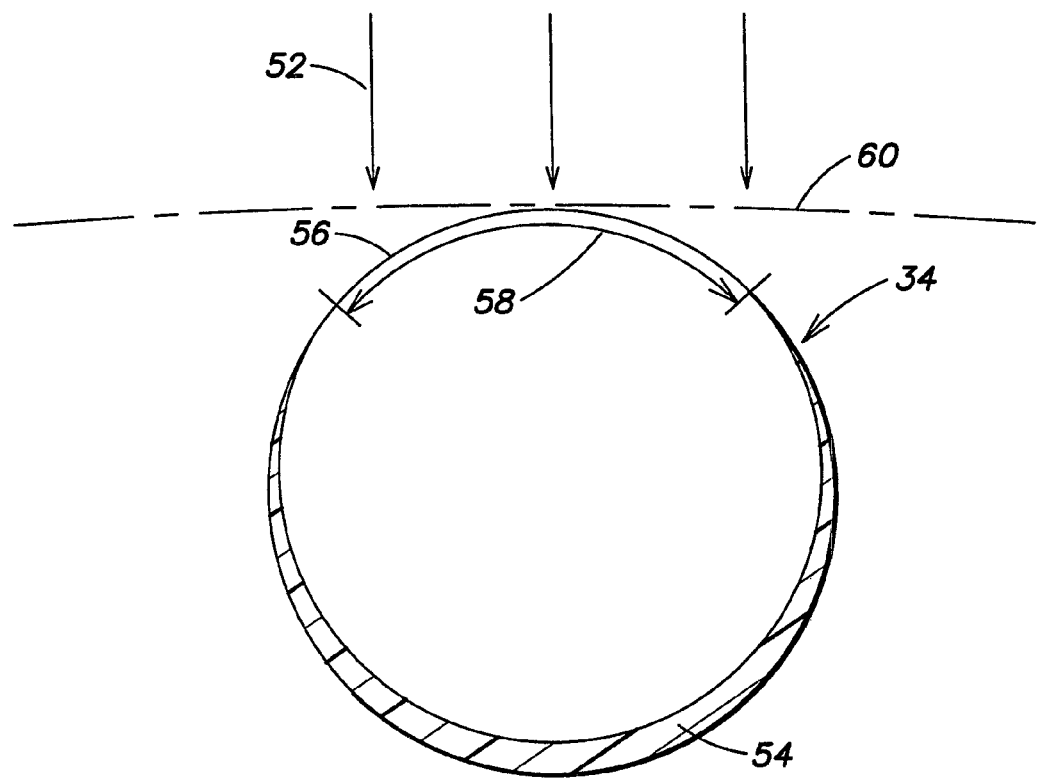

As illustrated particularly in FIGS. 4 and 5 a third sheath 32 may be provided. The third sheath serves to protect shaft portion 12 and in particular braided conductive member 28 during manipulation through the patient's vasculature. In addition, the third sheath 32 shields braided conductive member 28 from the patient's tissue in the event ablation energy is prematurely delivered to the braided conductive member 28.

The respective sheaths 24, 26, and 32 can be advanced and retracted over the inner member 22, which may be a tubular member, in many different manners. Control handle 14 may be used. U.S. Pat. Nos. 5,383,852, 5,462,527, and 5,611,777 illustrate examples of control handles that can control sheaths 24, 26, and 32. As described in these incorporated by reference patents, control handle 14 may include a slide actuator which is axially displaceable relative to the handle. The slide actuator may be connected to one of the sheaths, for example, the second sheath 26 to control the movement of the sheath 26 relative to inner member 22, to drive braided conductive member 28 between respective collapsed and deployed positions, as previously described. Control handle 14 may also include a second slide actuator or other mechanism coupled to the retractable outer sheath 32 to selectively retract the sheath in a proximal direction with respect to the inner member 22.

Braided conductive member 28 is, in one embodiment of the invention, a plurality of interlaced, electrically conductive filaments 34. Braided conductive member 28 may be a wire mesh. The filaments are flexible and capable of being expanded radially outwardly from inner member 22. The filaments 34 are preferably formed of metallic elements having relatively small cross sectional diameters, such that the filaments can be expanded radially outwardly. The filaments may be round, having a dimension on the order of about 0.001-0.030 inches in diameter. Alternatively, the filaments may be flat, having a thickness on the order of about 0.001-0.030 inches, and a width on the order of about 0.001-0.030 inches. The filaments may be formed of Nitinol type wire. Alternatively, the filaments may include non metallic elements woven with metallic elements, with the non metallic elements providing support to or separation of the metallic elements. A multiplicity of individual filaments 34 may be provided in braided conductive member 28, for example up to 300 or more filaments.

Each of the filaments 34 can be electrically isolated from each other by an insulation coating. This insulation coating may be, for example, a polyamide type material. A portion of the insulation on the outer circumferential surface 60 of braided conductive member 28 is removed. This allows each of the filaments 34 to form an isolated electrode, not an electrical contact with any other filament, that may be used for mapping and ablation. Alternatively, specific filaments may be permitted to contact each other to form a preselected grouping.

Each of the filaments 34 is helically wound under compression about inner member 22. As a result of this helical construction, upon radial expansion of braided conductive member 28, the portions of filaments 34 that have had the insulation stripped away do not contact adjacent filaments and thus, each filament 34 remains electrically isolated from every other filament. FIG. 6, in particular, illustrates how the insulation may be removed from individual filaments 34 while still providing isolation between and among the filaments. As illustrated in FIG. 6, regions 50 illustrate regions, on the outer circumferential surface 60 of braided conductive member 28, where the insulation has been removed from individual filaments 34. In one embodiment of the invention, the insulation may be removed from up to one half of the outer facing circumference of each of the individual filaments 34 while still retaining electrical isolation between each of the filaments 34.

The insulation on each of the filaments 34 that comprise braided conductive member 28 may be removed about the outer circumferential surface 60 of braided conductive member 28 in various ways. For example, one or more circumferential bands may be created along the length of braided conductive member 28. Alternatively, individual sectors or quadrants only may have their insulation removed about the circumference of braided conductive member 28. Alternatively, only selected filaments 34 within braided conductive member 28 may have their circumferentially facing insulation removed. Thus, an almost limitless number of configurations of insulation removal about the outer circumferential surface 60 of braided conductive member 28 can be provided depending upon the mapping and ablation characteristics and techniques that a clinician desires.

The insulation on each of the filaments 34 may be removed at the outer circumferential surface 60 of braided conductive member 28 in a variety of ways as long as the insulation is maintained between filaments 34 so that filaments 34 remain electrically isolated from each other.

The insulation can be removed from the filaments 34 in a variety of ways to create the stripped portions 50 on braided conductive member 28. For example, mechanical means such as abration or scraping may be used. In addition, a water jet, chemical means, or thermal radiation means may be used to remove the insulation.

In one example of insulation removal, braided conductive member 28 may be rotated about inner member 22, and a thermal radiation source such as a laser may be used to direct radiation at a particular point along the length of braided conductive member 28. As the braided conductive member 28 is rotated and the thermal radiation source generates heat, the insulation is burned off the particular region.

Insulation removal may also be accomplished by masking selected portions of braided conductive member 28. A mask, such as a metal tube may be placed over braided conducive member 28. Alternatively, braided conductive member 28 may be wrapped in foil or covered with some type of photoresist. The mask is then removed in the areas in which insulation removal is desired by, for example, cutting away the mask, slicing the foil, or removing the photoresist. Alternatively, a mask can be provided that has a predetermined insulation removal pattern. For example, a metal tube having cutouts that, when the metal tube is placed over braided conductive member 28, exposes areas where insulation is to be removed.

FIG. 6 illustrates how thermal radiation 52 may be applied to the outer circumferential surface 56 of a respective filament 34 that defines the outer circumferential surface 60 of braided conductive member 28. As thermal radiation 52 is applied, the insulation 54 is burned off or removed from the outer circumference 56 of wire 34 to create a region 58 about the circumference 56 of filament 34 that has no insulation.

The insulation 54 can also be removed in a preferential manner so that a particular portion of the circumferential surface 56 of a filament 34 is exposed. Thus, when braided conductive member 28 is radially expanded, the stripped portions of filaments may preferentially face the intended direction of mapping or ablation.

With the insulation removed from the portions of filaments 34 on the outer circumferential surface 60 of braided conductive member 28, a plurality of individual mapping and ablation channels can be created. A wire runs from each of the filaments 34 within catheter shaft 12 and control handle 14 to connector portion 16. A multiplexer or switch box may be connected to the conductors so that each filament 34 may be controlled individually. This function may be incorporated into controller 8. A number of filaments 34 may be grouped together for mapping and ablation. Alternatively, each individual filament 34 can be used as a separate mapping channel for mapping individual electrical activity within a blood vessel at a single point. Using a switch box or multiplexer to configure the signals being received by filaments 34 or ablation energy sent to filaments 34 results in an infinite number of possible combinations of filaments for detecting electrical activity during mapping procedures and for applying energy during an ablation procedure.

By controlling the amount of insulation that is removed from the filaments 34 that comprise braided conductive member 28, the surface area of the braid that is in contact with a blood vessel wall can also be controlled. This in turn will allow control of the impedance presented to an ablation energy generator, for example, generator 4. In addition, selectively removing the insulation can provide a predetermined or controllable profile of the ablation energy delivered to the tissue.

The above description illustrates how insulation may be removed from a filaments 34. Alternatively, the same features and advantages can be achieved by adding insulation to filaments 34. For example, filaments 34 may be bare wire and insulation can be added to them.

Individual control of the electrical signals received from filaments 34 allows catheter 10 to be used for bipolar (differential or between filament) type mapping as well as unipolar (one filament with respect to a reference) type mapping.

Catheter 10 may also have, as illustrated in FIGS. 2 and 3, a reference electrode 13 mounted on shaft 12 so that reference electrode 13 is located outside the heart during unipolar mapping operations.

Radiopaque markers can also be provided for use in electrode orientation and identification.

One skilled in the art will appreciate all of the insulation can be removed from filaments 34 to create a large ablation electrode.

Although a complete catheter steerable structure has been illustrated, the invention can also be adapted so that inner tubular member 22 is a catheter shaft, guide wire, or a hollow tubular structure for introduction of saline, contrast media, heparin or other medicines, or introduction of guidewires, or the like.

Temperature Sensing

A temperature sensor or sensors, such as, but not limited to, one or more thermocouples may be attached to braided conductive member 28 for temperature sensing during ablation procedures. A plurality of thermocouples may also be woven into the braided conductive member 28. An individual temperature sensor could be provided for each of the filaments 34 that comprise braided conductive member 28. Alternatively, braided conductive member 28 can be constructed of one or more temperature sensors themselves.

Figure 8:
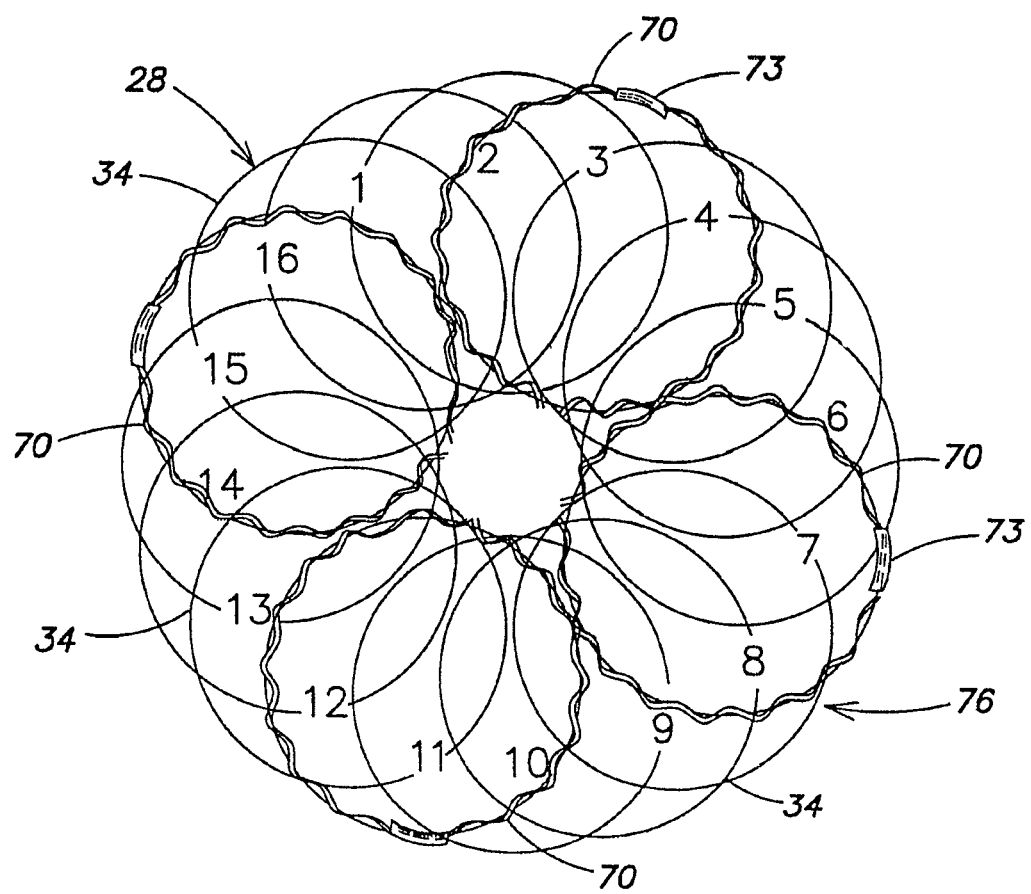
Figure 9:
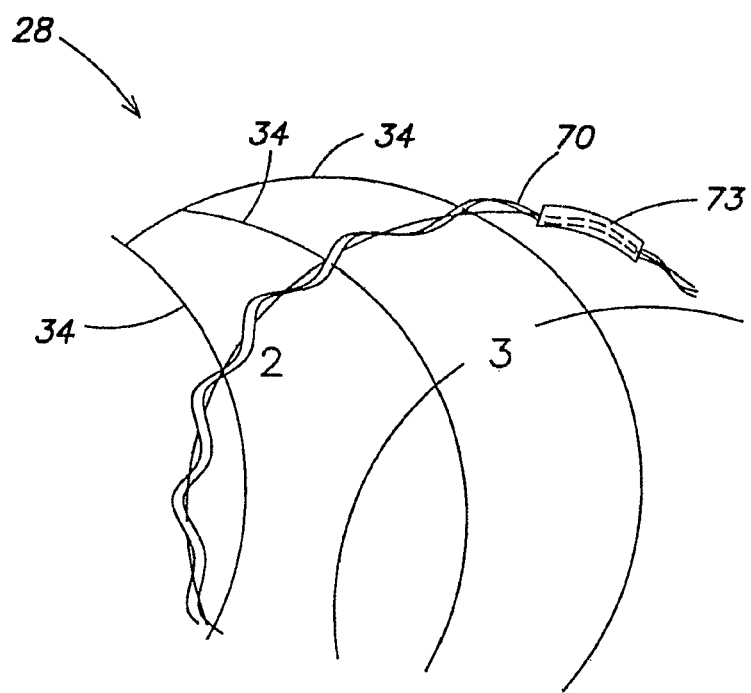

FIG. 8 illustrates braided conductive member 28 in its fully expanded or deployed configuration. Braided conductive member 28 forms a disk when fully expanded. In the embodiment illustrated in FIG. 8, there are sixteen filaments 34 that make up braided conductive member 28.

Temperature monitoring or control can be incorporated into braided conductive member 28, for example, by placing temperature sensors (such as thermocouples, thermistors, etc.) on the expanded braided conductive member 28 such that they are located on the distally facing ablative ring formed when braided conductive member 28 is in its fully expanded configuration. "Temperature monitoring" refers to temperature reporting and display for physician interaction. "Temperature control" refers to the capability of adding an algorithm in a feedback loop to titrate power based on temperature readings from the temperature sensors disposed on braided conductive member 28. Temperature sensors can provide a means of temperature control provided the segment of the ablative ring associated with each sensor is independently controllable (e.g., electrically isolated from other regions of the mesh). For example, control can be achieved by dividing the ablative structure into electrically independent sectors, each with a temperature sensor, or alternatively, each with a mechanism to measure impedance in order to facilitate power titration. The ablative structure may be divided into electrically independent sectors so as to provide zone control. The provision of such sectors can be used to provide power control to various sections of braided conductive member 28.

As illustrated in FIG. 8, four temperature sensors 70 are provided on braided conductive member 28. As noted previously, since the individual filaments 34 in braided conductive member 28 are insulated from each other, a number of independent sectors may be provided. A sector may include one or more filaments 34. During ablation procedures, energy can be applied to one or more of the filaments 34 in any combination desired depending upon the goals of the ablation procedure. A temperature sensor could be provided on each filament 34 of braided conductive member 28 or shared among one or more filaments. In mapping applications, one or more of the filaments 34 can be grouped together for purposes of measuring electrical activity. These sectoring functions can be provided in controller 8.

FIG. 10 illustrates a side view of braided conductive member 28 including temperature sensors 70. As shown in FIG. 10, temperature sensors 70 emerge from four holes 72. Each hole 72 is disposed in one quadrant of anchor 74. The temperature sensors 70 are bonded to the outside edge 76 of braided conductive member 28. Temperature sensors 70 may be isolated by a small piece of polyimide tubing 73 around them and then bonded in place to the filaments. The temperature sensors 7 may be woven and twisted into braided conductive member 28 or they can be bonded on a side-by-side or parallel manner with the filaments 34.

There are several methods of implementing electrically independent sectors. In one embodiment, the wires are preferably stripped of their insulative coating in the region forming the ablative ring (when expanded). However, sufficient insulation may be left on the wires in order to prevent interconnection when in the expanded state. Alternatively, adjacent mesh wires can be permitted to touch in their stripped region, but can be separated into groups by fully insulated (unstripped) wires imposed, for example, every 3 or 5 wires apart (the number of wires does not limit this invention), thus forming sectors of independently controllable zones. Each zone can have its own temperature sensor. The wires can be "bundled" (or independently attached) to independent outputs of an ablation energy generator. RF energy can then be titrated in its application to each zone by switching power on and off (and applying power to other zones during the 'off period') or by modulating voltage or current to the zone (in the case of independent controllers). In either case, the temperature inputs from the temperature sensors can be used in a standard feedback algorithm to control the power delivery.

Figure 10A:
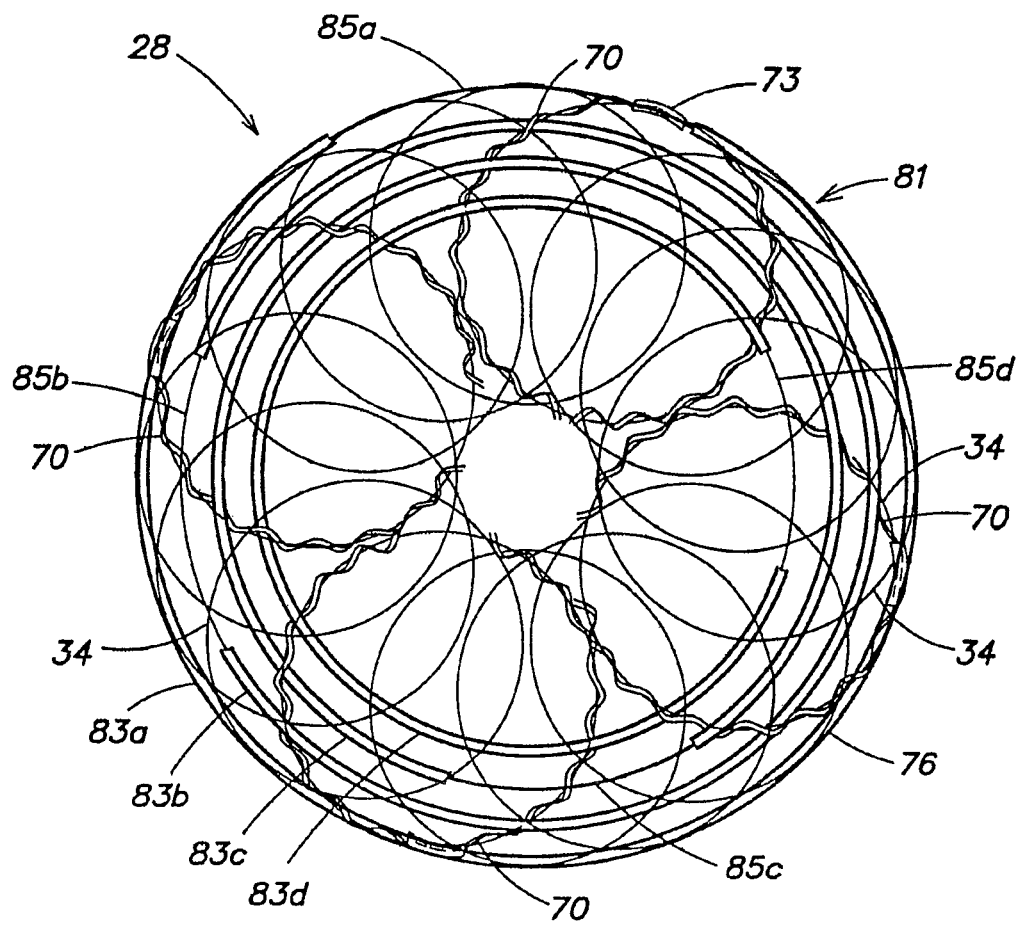

Alternatively, as illustrated in FIG. 10A, braided conductive member 28 may be used to support a ribbon-like structure which is separated into discrete sectors. As shown in FIG. 10A, the ribbon-like structure 81 may be, for example, a pleated copper flat wire that, as braided conductive member 28 expands, unfolds into an annular ring. Each of the wires 83a-83d lie in the same plane. Although four wires are illustrated in FIG. 10A, structure 81 may include any number of wires depending upon the application and desired performance. Each of wires 83a-83d is insulated. Insulation may then be removed from each wire to create different sectors 85a-85d. Alternatively, each of wires 83a-83d may be uninsulated and insulation may be added to create different sectors. The different sectors provide an ablative zone comprised of independently controllable wires 83a-83d. Temperature sensors 70 may be mounted on the individual wires, and filaments 34 may be connected to respective wires 83a-83d to provide independent control of energy to each individual sector. One skilled in the art will appreciate that each of wires 83a-83d can have multiple sectors formed by removing insulation in various locations and that numerous combinations of sectors 85a-85d and wires 83a-83d forming ribbon-like structure 81 can be obtained.

Steering

Figure 11:
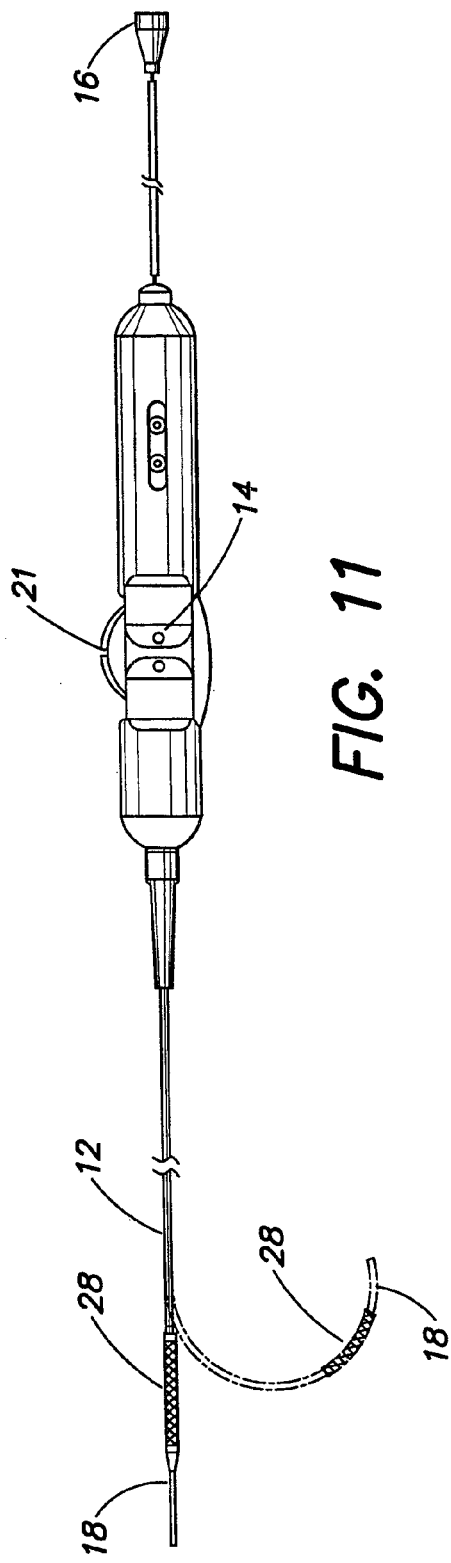
FIGS. 11-13 illustrate further details of the steering capabilities of the present invention.
Figure 12:
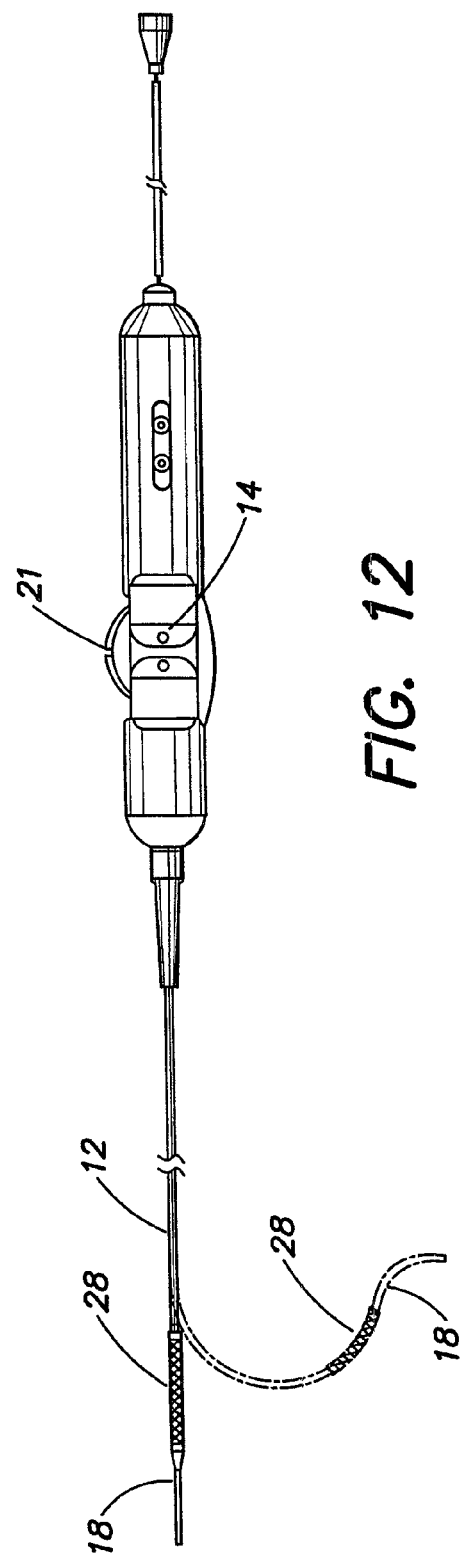
Figure 13:
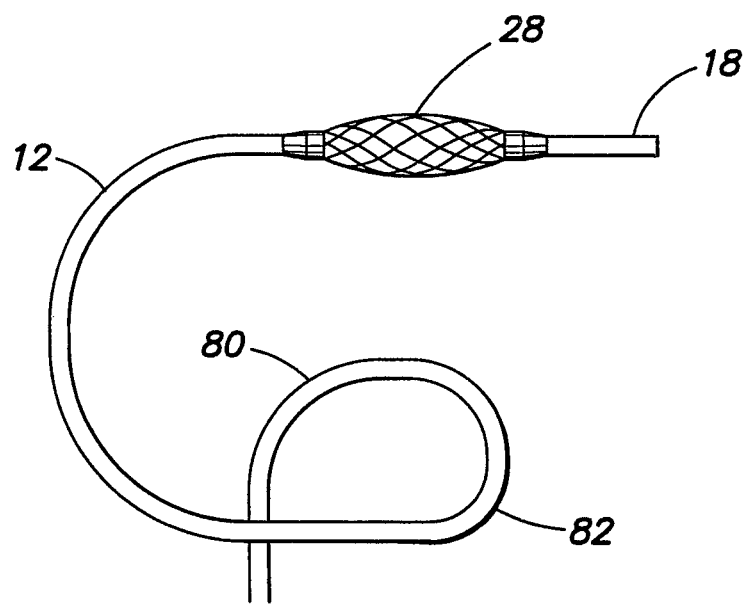

Reference is now made to FIGS. 11-13 which illustrate aspects of the steering capabilities of the present invention. As illustrated in FIGS. 1-2, catheter 10 is capable of being steered using control handle 14. In particular, FIG. 1 illustrates steering where the steering pivot or knuckle is disposed on catheter shaft 12 in a region that is distal to the braided conductive member 28.

FIG. 11 illustrates catheter 10 wherein the pivot point or steering knuckle is disposed proximal to braided conductive member 28.

FIG. 12 illustrates catheter 10 having the capability of providing steering knuckles both proximal and distal to braided conductive member 28.

FIGS. 1-2, and 11-12 illustrate two dimensional or single plane type steering. The catheter of the present invention can also be used in connection with a three dimensional steering mechanism. For example, using the control handle in the incorporated by reference '852 patent, the catheter can be manipulated into a three-dimensional "lasso-like" shape, particularly at the distal end of the catheter. As shown in FIG. 13, the catheter can have a primary curve 80 in one plane and then a second curve 82 in another plane at an angle to the first plane. With this configuration, the catheter can provide increased access to difficult to reach anatomical structures. For example, a target site for a mapping or ablation operation may be internal to a blood vessel. Thus, the increased steering capability can allow easier access into the target blood vessel. In addition, the additional dimension of steering can allow for better placement of braided conductive member 28 during an ablation or mapping procedure. Catheter 10 can be inserted into a site using the steering capabilities provided by primary curve 80. Thereafter, using the secondary curve 82, braided conductive member 28 can be tilted into another plane for better orientation or contact with the target site.

Conductive Member Configurations and Materials

Reference is now made to FIGS. 14-17 which figures illustrate other configurations of braided conductive member 28. As has been described above and will be described in more detail, braided conductive member 28 can include from one to 300 or more filaments. The filaments may vary from very fine wires having small diameters or cross-sectional areas to large wires having relatively large diameters or cross-sectional areas.

Figure 14:
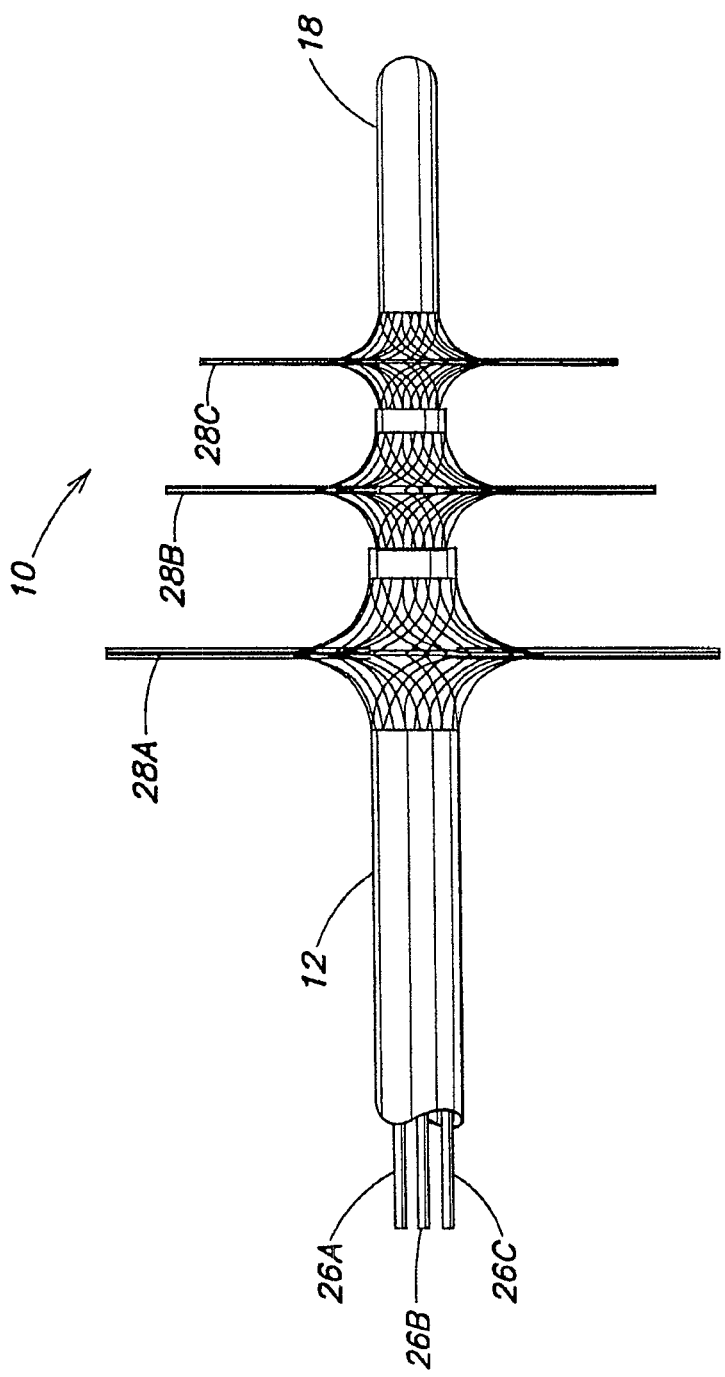
FIGS. 14-17 illustrate further embodiments of the braided conductive member.

FIG. 14 illustrates the use of more than one braided conductive member 28 as the distal end of catheter 10. As shown in FIG. 14, three braided conductive members 28A, 28B, and 28C are provided at the distal end of catheter 10. Braided conductive members 28A, 28B, and 29C may be, in their expanded conditions, the same size or different sizes. Each of the braided conductive members 28A, 28B, and 28C can be expanded or contracted independently in the manner illustrated in FIGS. 1-4 via independent control shafts 26A, 26B, and 26C. The use of multiple braided conductive members provides several advantages. Rather than having to estimate or guess as to the size of the blood vessel prior to starting a mapping or ablation procedure, if braided conductive members 28A, 28B, and 28C are of different expanded diameters, than sizing can be done in vivo during a procedure. In addition, one of the braided conductive members can be used for ablation and another of the braided conductive members can be used for mapping. This allows for quickly checking the effectiveness of an ablation procedure.

Figure 15A:
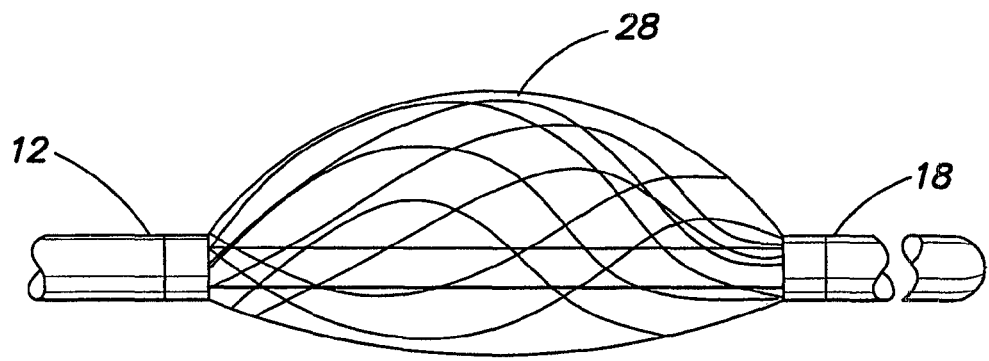
Figure 15B:
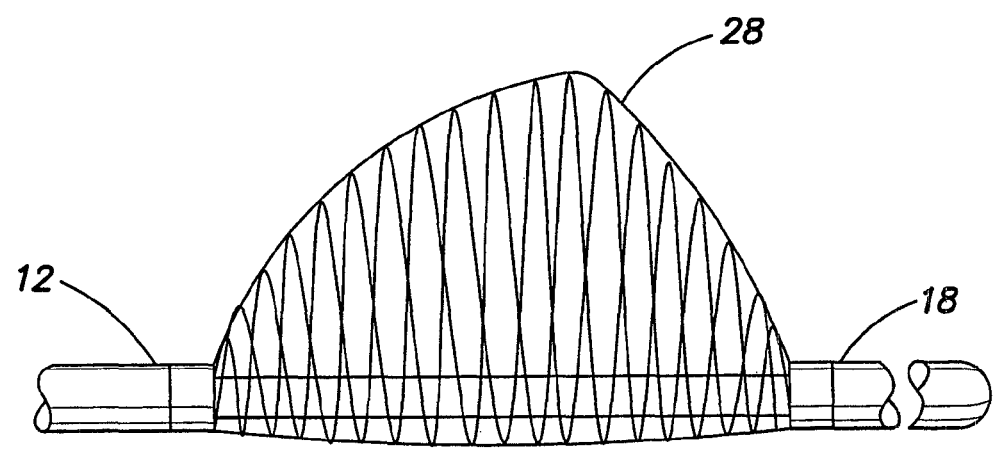

Reference is now made to FIGS. 15A and 15B, which figures illustrate other shapes of braided conductive member 28. As described up to this point, braided conductive member 28 is generally symmetrical and coaxial with respect to catheter shaft 12. However, certain anatomical structures may have complex three-dimensional shapes that are not easily approximated by a geometrically symmetrical mapping or ablation structure. One example of this type of structure occurs at the CS ostium. To successfully contact these types of anatomical structures, braided conductive member 28 can be "preformed" to a close approximation of that anatomy, and yet still be flexible enough to adapt to variations found in specific patients. Alternatively, braided conductive member 28 can be "preformed" to a close approximation of that anatomy, and be of sufficient strength (as by choice of materials, configuration, etc.) to force the tissue to conform to variations found in specific patients. For example FIG. 15A illustrates braided conductive member 28 disposed about shaft 12 in an off-center or non concentric manner. In addition, braided conductive member 28 may also be constructed so that the parameter of the braided conductive member in its expanded configuration has a non-circular edge so as to improve tissue contact around the parameter of the braided conductive member. FIG. 15B illustrates an example of this type of configuration where the braided conductive member 28 is both off center or non concentric with respect to catheter shaft 12 and also, in its deployed or expanded configuration, has an asymmetric shape. The eccentricity of braided conductive member 28 with respect to the shaft and the asymmetric deployed configurations can be produced by providing additional structural supports in braided conductive member 28, for example, such as by adding nitinol, ribbon wire, and so on. In addition, varying the winding pitch or individual filament size or placement or deforming selective filaments in braided conductive member 28 or any other means known to those skilled in the art may be used.

Figure 16A:
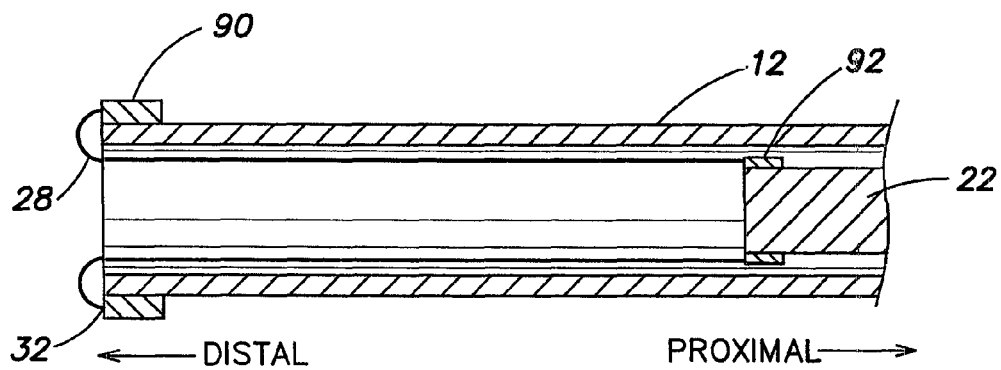
Figure 16B:
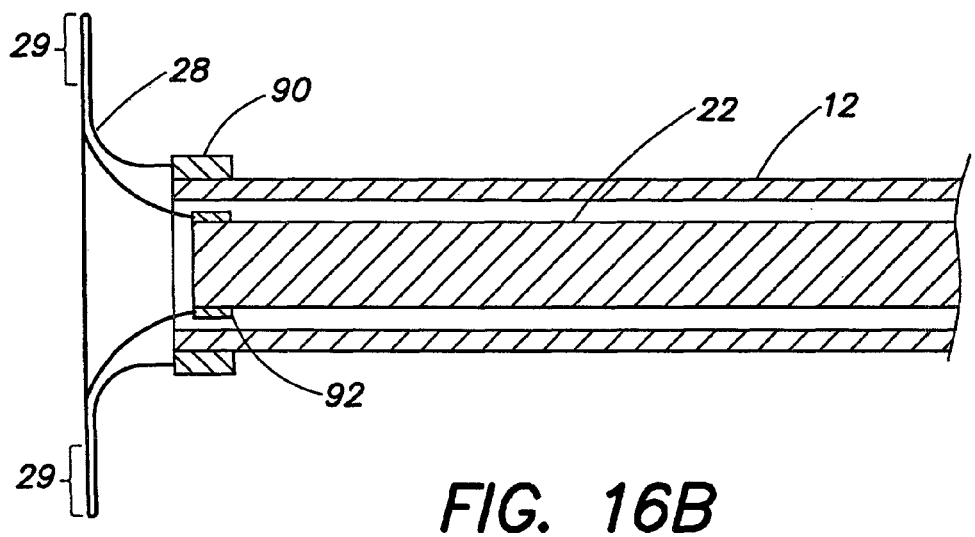
Figure 16C:
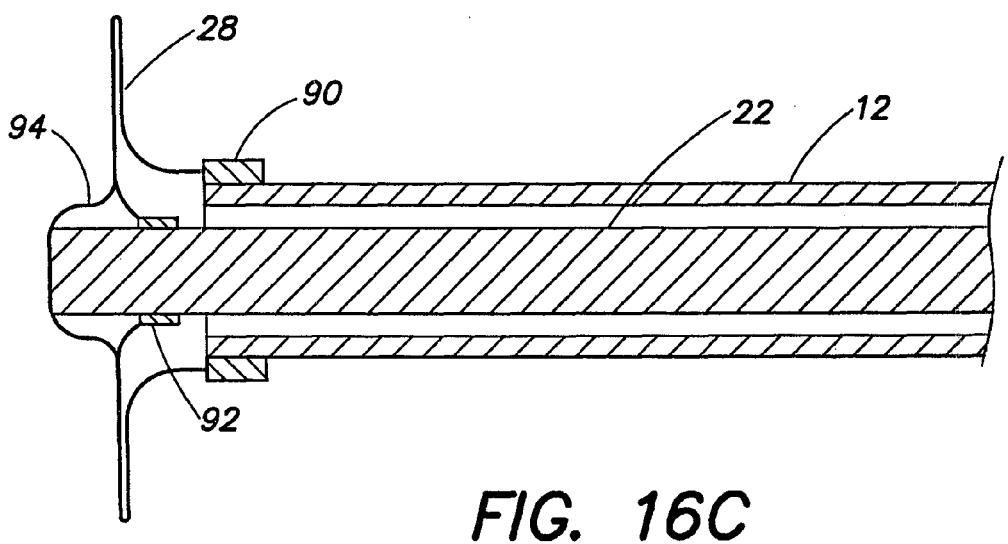

FIGS. 16A-16C illustrate another configuration of braided conductive member 28 and catheter 10. As illustrated in FIGS. 16A-16C, the distal tip section of catheter 10 has been removed and braided conductive member 28 is disposed at the distal end of catheter 10. One end of braided conductive member 28 is anchored to catheter shaft 12 using an anchor band 90 that clamps the end 32 of braided conductive member 28 to catheter shaft 12. The other end of braided conductive member 28 is clamped to an activating shaft such as shaft 22 using another anchor band 92. FIG. 16A illustrates braided conductive member 28 in its undeployed configuration. As shaft 22 is moved distally, braided conductive member 28 emerges or everts from shaft 12. As shown in FIG. 16B, braided conductive member 28 has reached its fully deployed diameter and an annular tissue contact zone 29 can be placed against an ostium or other anatomical structure. As illustrated in FIG. 16C, further distal movement of shaft 22 can be used to create a concentric locating region 94 that can help to provide for concentric placement within an ostium of a pulmonary vein, for example. Concentric locating region 94 may be formed by selective variations in the winding density of filaments 34 in braided conductive member 28, preferential predeformation of the filaments, additional eversion of braided conductive member 28 from shaft 12, or by other means known to those skilled in the art.

Figure 17:
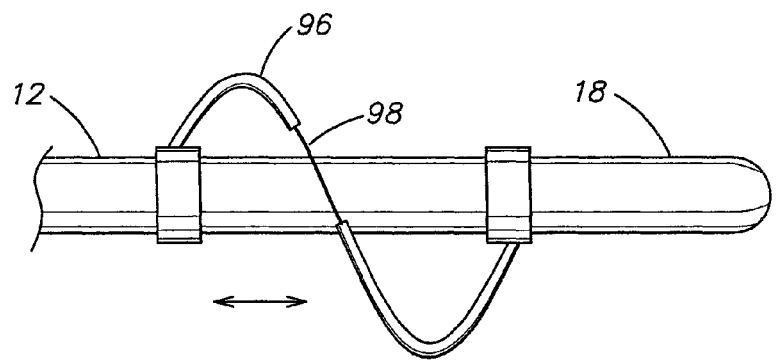

Reference is now made to FIG. 17, which figure illustrates a further embodiment of braided conductive member 28. As illustrated in FIG. 17, braided conductive member 28 is composed of one or several large wires 96 rather than a multiplicity of smaller diameter wires. The wire or wires can be moved between the expanded and unexpanded positions in the same manner as illustrated in FIG. 1. In addition, a region 98 may be provided in which the insulation has been removed for mapping or ablation procedures. The single wire or "corkscrew" configuration provides several advantages. First, the wire or wires do not cross each other and therefore there is only a single winding direction required for manufacture. In addition, the risk of thrombogenicity may be reduced because there is a smaller area of the blood vessel being blocked. In addition, the connections between the ends of the large wire and the control shafts may be simplified.

The catheter 10 of the present invention can be coated with a number of coatings that can enhance the operating properties of braided conductive member 28. The coatings can be applied by any of a number of techniques and the coatings may include a wide range of polymers and other materials.

Braided conductive member 28 can be coated to reduce its coefficient of friction, thus reducing the possibility of thrombi adhesion to the braided conductive member as well as the possibility of vascular or atrial damage. These coatings can be combined with the insulation on the filaments that make up braided conductive member 28, these coatings can be included in the insulation itself, or the coatings can be applied on top of the insulation. Examples of coating materials that can be used to improve the lubricity of the catheter include PD slick available from Phelps Dodge Corporation, Ag, Tin, BN. These materials can be applied by an ion beam assisted deposition ("IBAD") technique developed by, for example, Amp Corporation.

Braided conductive member 28 can also be coated to increase or decrease its thermal conduction which can improve the safety or efficacy of the braided conductive member 28. This may be achieved by incorporating thermally conductive elements into the electrical insulation of the filaments that make up braided conductive member 28 or as an added coating to the assembly. Alternatively, thermally insulating elements may be incorporated into the electrical insulation of the filaments that make up braided conductive member 28 or added as a coating to the assembly. Polymer mixing, IBAD, or similar technology could be used to add Ag, Pt, Pd, Au, Ir, Cobalt, and others into the insulation or to coat braided conductive member 28.

Radioopaque coatings or markers can also be used to provide a reference point for orientation of braided conductive member 28 when viewed during fluoroscopic imaging. The materials that provide radiopacity including, for example, Au, Pt, Ir, and other known to those skilled in the art. These materials may be incorporated and used as coatings as described above.

Antithrombogenic coatings, such as heparin and BH, can also be applied to braided conductive member 28 to reduce thrombogenicity to prevent blood aggregation on braided conductive member 28. These coatings can be applied by dipping or spraying, for example.

As noted above, the filament 34 of braided conductive member 28 may be constructed of metal wire materials. These materials may be, for example, MP35N, nitinol, or stainless steel. Filaments 34 may also be composites of these materials in combination with a core of another material such as silver or platinum. The combination of a highly conductive electrical core material with another material forming the shell of the wire allows the mechanical properties of the shell material to be combined with the electrical conductivity of the core material to achieve better and/or selectable performance. The choice and percentage of core material used in combination with the choice and percentage of shell material used can be selected based on the desired performance characteristics and mechanical/electrical properties desired for a particular application.

Irrigation

Figure 18:
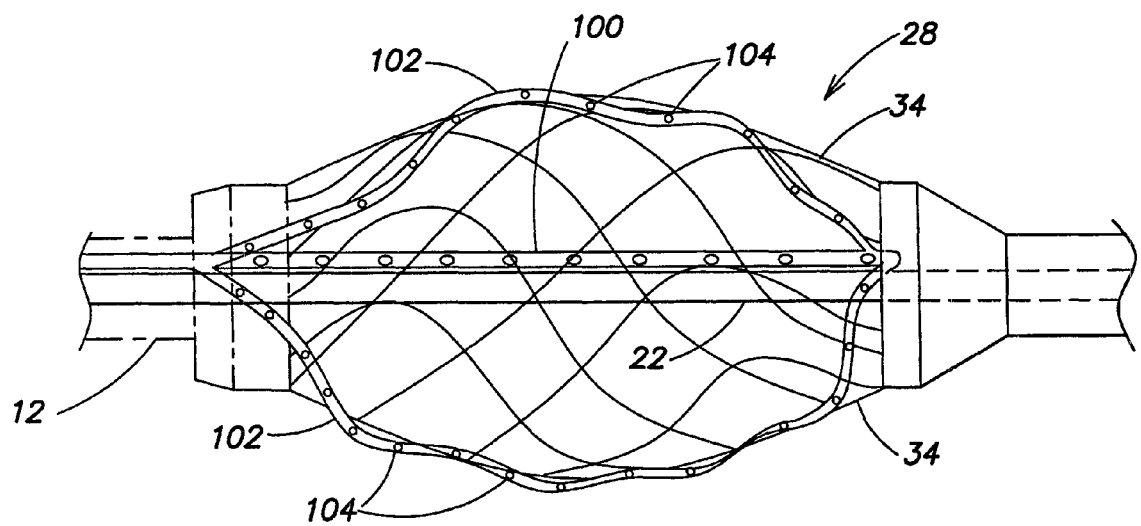

It is known that for a given electrode side and tissue contact area, the size of a lesion created by radiofrequency (RF) energy is a function of the RF power level and the exposure time. At higher powers, however, the exposure time can be limited by an increase in impedance that occurs when the temperature at the electrode-tissue interface approaches a 100° C. One way of maintaining the temperature less than or equal to this limit is to irrigate the ablation electrode with saline to provide convective cooling so as to control the electrode-tissue interface temperature and thereby prevent an increase in impedance. Accordingly, irrigation of braided conductive member 28 and the tissue site at which a lesion is to be created can be provided in the present invention. FIG. 18 illustrates the use of an irrigation manifold within braided conductive member 28. An irrigation manifold 100 is disposed along shaft 22 inside braided conductive member 28. Irrigation manifold 100 may be one or more polyimid tubes. Within braided conductive member 28, the irrigation manifold splits into a number of smaller tubes 102 that are woven into braided conductive member 28 along a respective filament 34. A series of holes 104 may be provided in each of the tubes 102. These holes can be oriented in any number of ways to target a specific site or portion of braided conductive member 28 for irrigation. Irrigation manifold 100 runs through catheter shaft 12 and may be connected to an irrigation delivery device outside the patient used to inject an irrigation fluid, such as saline, for example, such as during an ablation procedure.

The irrigation system can also be used to deliver a contrast fluid for verifying location or changes in vessel diameter. For example, a contrast medium may be perfused prior to ablation and then after an ablation procedure to verify that there have been no changes in the blood vessel diameter. The contrast medium can also be used during mapping procedures to verify placement of braided conductive member 28. In either ablation or mapping procedures, antithrombogenic fluids, such as heparin can also be perfused to reduce thrombogenicity.

FIG. 19 illustrates another way of providing perfusion/irrigation in catheter 10. As illustrated in FIG. 19, the filaments 34 that comprise braided conductive member 28 are composed of a composite wire 110. The composite wire 110 includes an electrically conductive wire 112 that is used for delivering ablation energy in an ablation procedure or for detecting electrical activity during a mapping procedure. Electrical wire 112 is contained within a lumen 114 that also contains a perfusion lumen 116. Perfusion lumen 116 is used to deliver irrigation fluid or a contrast fluid as described in connection with FIG. 18. Once braided conductive member 28 has been constructed with composite wire 110, the insulation 118 surrounding wire filament 112 can be stripped away to form an electrode surface. Holes can then be provided into perfusion lumen 116 to then allow perfusion at targeted sites along the electrode surface. As with the embodiment illustrated in FIG. 18, the perfusion lumens can be connected together to form a manifold which manifold can then be connected to, for example, perfusion tube 120 and connected to a fluid delivery device.

Shrouds

The use of a shroud or shrouds to cover at least a portion of braided conductive member 28 can be beneficial in several ways. The shroud can add protection to braided conductive member 28 during insertion and removal of catheter 10. A shroud can also be used to form or shape braided conductive member 28 when in its deployed state. Shrouds may also reduce the risk of thrombi formation on braided conductive member 28 by reducing the area of filament and the number of filament crossings exposed to blood contact. This can be particularly beneficial at the ends 30 and 32 of braided conductive member 28. The density of filaments at ends 30 and 32 is greatest and the ends can therefore be prone to blood aggregation. The shrouds can be composed of latex balloon material or any material that would be resistant to thrombi formation durable enough to survive insertion through an introducer system, and would not reduce the mobility of braided conductive member 28. The shrouds can also be composed of an RF transparent material that would allow RF energy to pass through the shroud. If an RF transparent material is used, complete encapsulation of braided conductive member 28 is possible.

A shroud or shrouds may also be useful when irrigation or perfusion is used, since the shrouds can act to direct irrigation or contrast fluid to a target region.

Figure 20A:
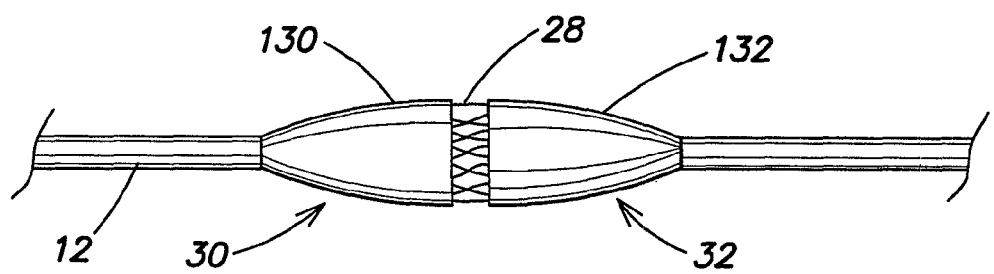
FIGS. 20A-20E illustrate the use of shrouds in the present invention.
Figure 20B:
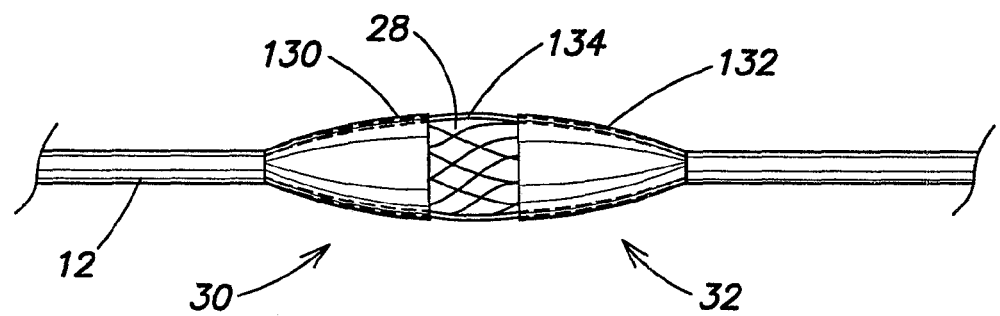

FIGS. 20A-20E illustrate various examples of shrouds that may be used in the present invention. FIG. 20A illustrates shrouds 130 and 132 disposed over end regions 31 and 33, respectively, of braided conductive member 28. This configuration can be useful in preventing coagulation of blood at the ends of braided conductive member 28. FIG. 20B illustrates shrouds 130 and 132 used in conjunction with an internal shroud 134 contained inside braided conductive member 28. In addition to preventing blood coagulation in regions 31 and 32, the embodiment illustrated in FIG. 20B also prevents blood from entering braided conductive member 28.

Figure 20C:
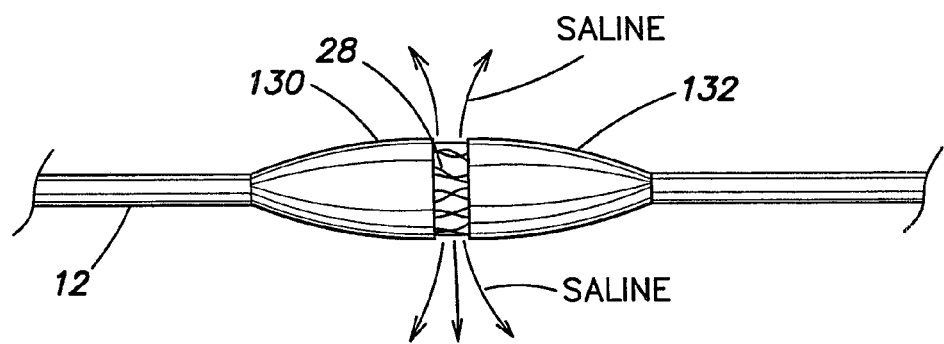

FIG. 20C illustrates shrouds 130 and 132 being used to direct and irrigation fluid or contrast medium along the circumferential edge of braided conductive member 28. In the embodiment illustrated in FIG. 20C, perfusion can be provided as illustrated in FIGS. 18 and 19.

Figure 20D:
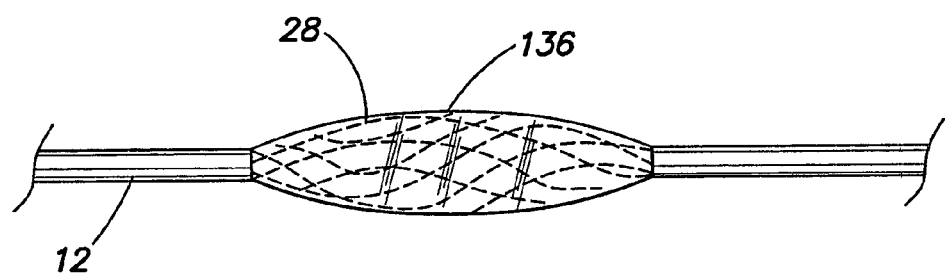

FIG. 20D illustrates the use of an external shroud that covers braided conductive member 28. Shroud 136 completely encases braided conductive member 28 and thereby eliminates blood contact with braided conductive member 28. Shroud 136 may be constructed of a flexible yet ablation-energy transparent material so that, when used in an ablation procedure, braided conductive member 28 can still deliver energy to a targeted ablation site.

Figure 20E:
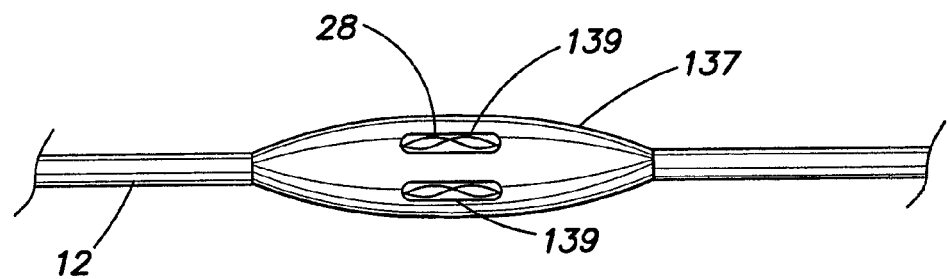

FIG. 20E also illustrates an external shroud 137 encasing braided conductive member 28. Shroud 137 may also be constructed of a flexible yet ablation-energy transparent material. Openings 139 may be provided in shroud 137 to allow the portions of braided conductive member 28 that are exposed by the opening to come into contact with tissue. Openings 139 may be elliptical, circular, circumferential, etc.

Guiding Sheaths

There may be times during ablation or mapping procedures when catheter 10 is passing through difficult or tortuous vasculature. During these times, it may be helpful to have a guiding sheath through which to pass catheter 10 so as to allow easier passage through the patient's vasculature.

Figure 21:
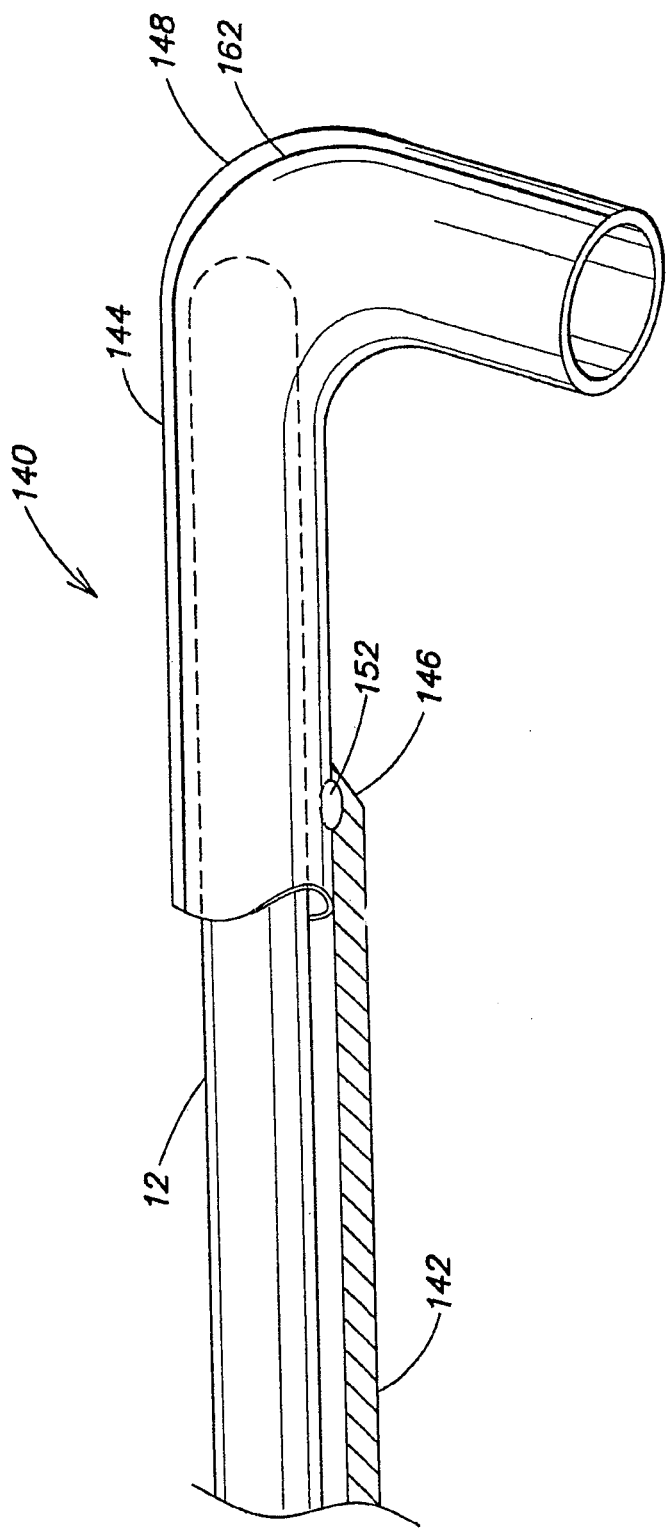
FIG. 21 illustrates a guiding sheath that may be used in connection with the present invention.

FIG. 21 illustrates one example of a guiding sheath that may be used in connection with catheter 10. As illustrated in FIG. 21, the guiding sheath 140 includes a longitudinal member 142. Longitudinal member 142 may be constructed of a material rigid enough to be pushed next to catheter shaft 12 as the catheter is threaded through the vasiculature. In one example, longitudinal member 142 may be stainless steel. Longitudinal member 142 is attached to a sheath 144 disposed at the distal end 146 of longitudinal member 142. The split sheath 144 may have one or more predetermined curves 148 that are compatible with the shapes of particular blood vessels (arteries or veins) that catheter 10 needs to pass through. Split sheath 144 may extend proximally along longitudinal member 142. For example, sheath 144 and longitudinal member 142 may be bonded together for a length of up to 20 or 30 centimeters to allow easier passage through the patient's blood vessels. Sheath 144 includes a predetermined region 150 that extends longitudinally along sheath 144. Region 150 may be, for example, a seam, that allows sheath 144 to be split open so that the guiding sheath 140 can be pulled back and peeled off catheter shaft 12 in order to remove the sheath.

In another embodiment, longitudinal member 142 may be a hypotube or the like having an opening 152 at distal end 146 that communicates with the interior of sheath 144. In this embodiment, longitudinal member 142 can be used to inject irrigation fluid such as saline or a contrast medium for purposes of cooling, flushing, or visualization.

Methods of Use

Figure 22:
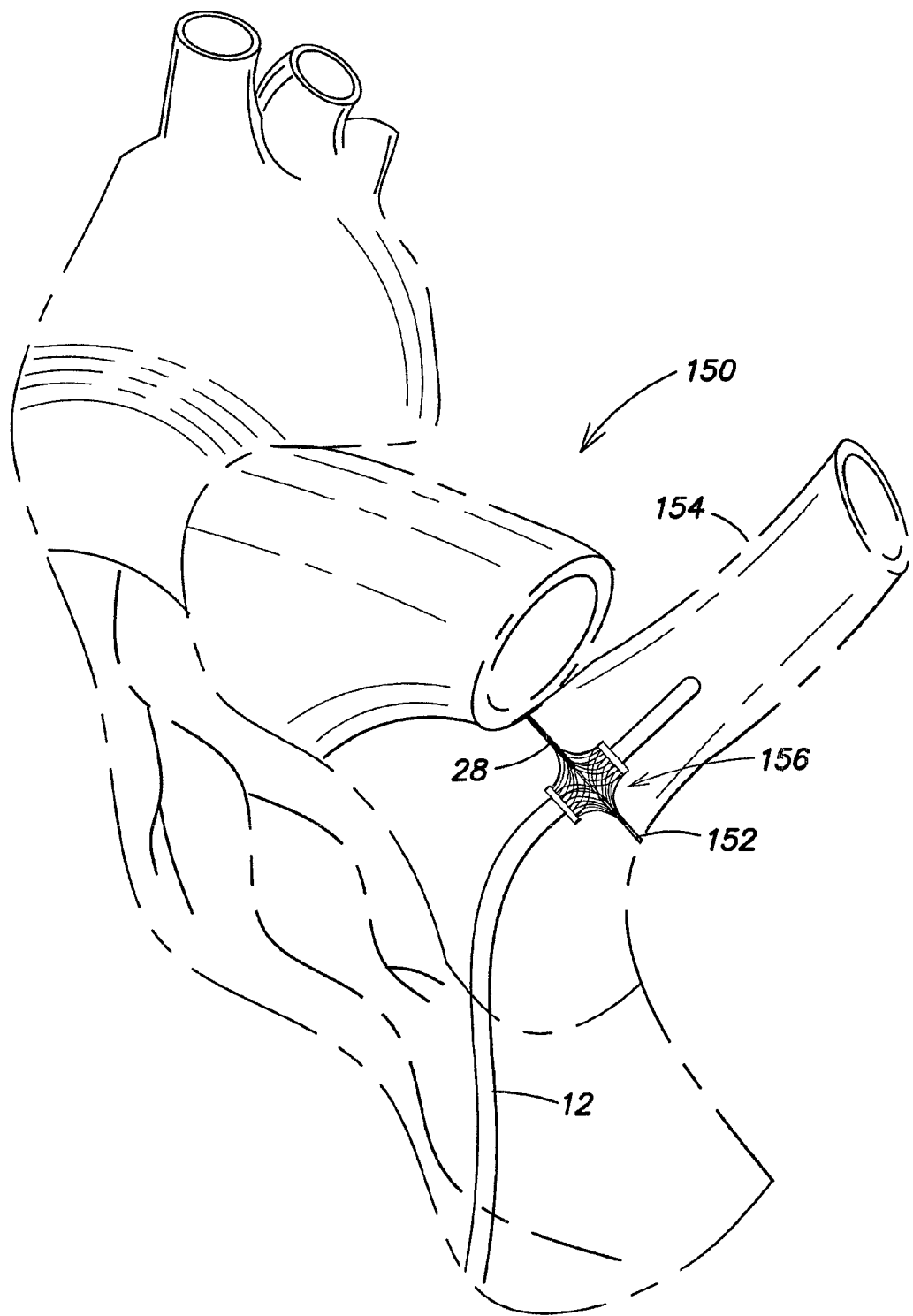
FIGS. 22-24 illustrate methods of using the present invention.
Figure 23:
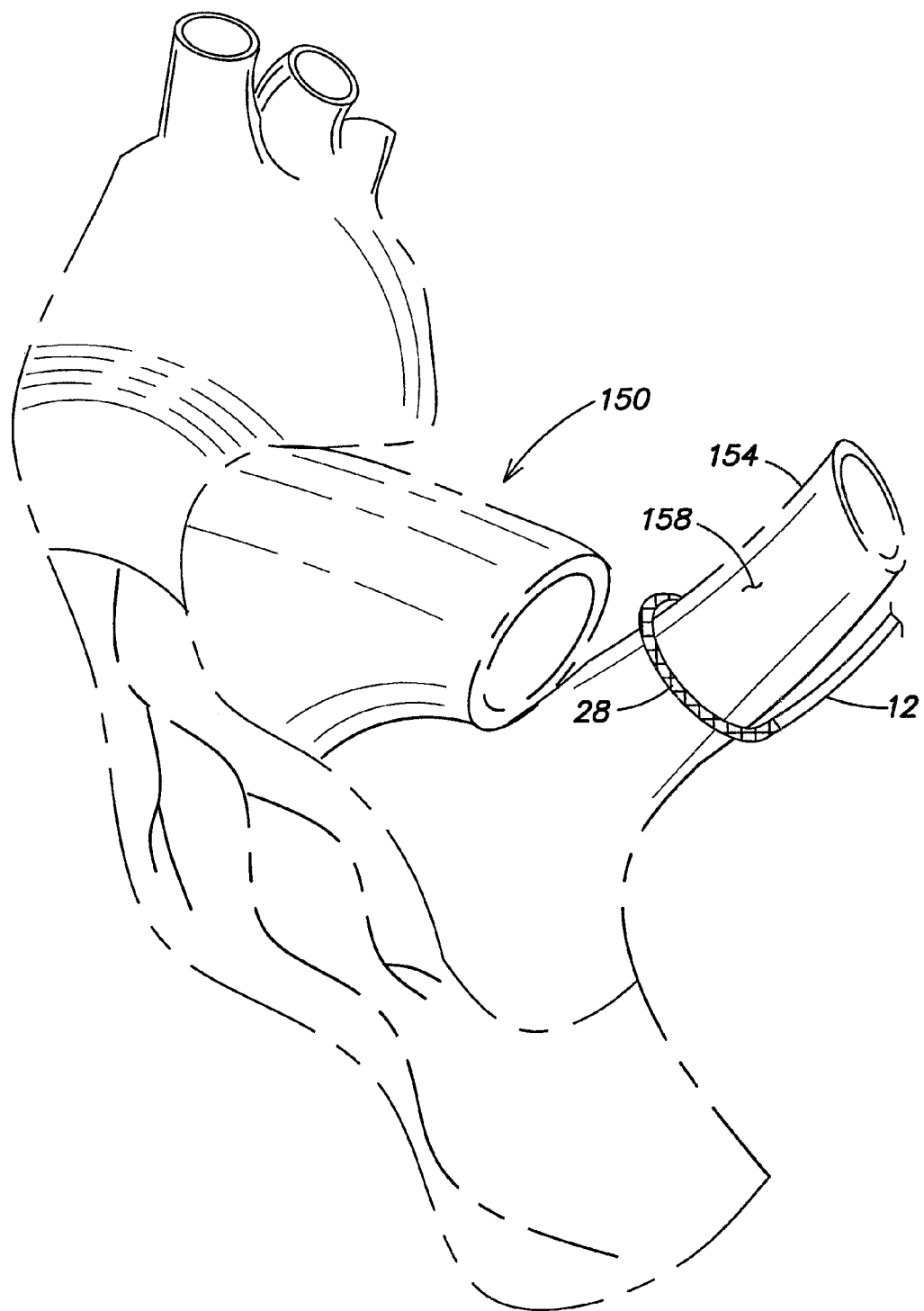
Figure 24:
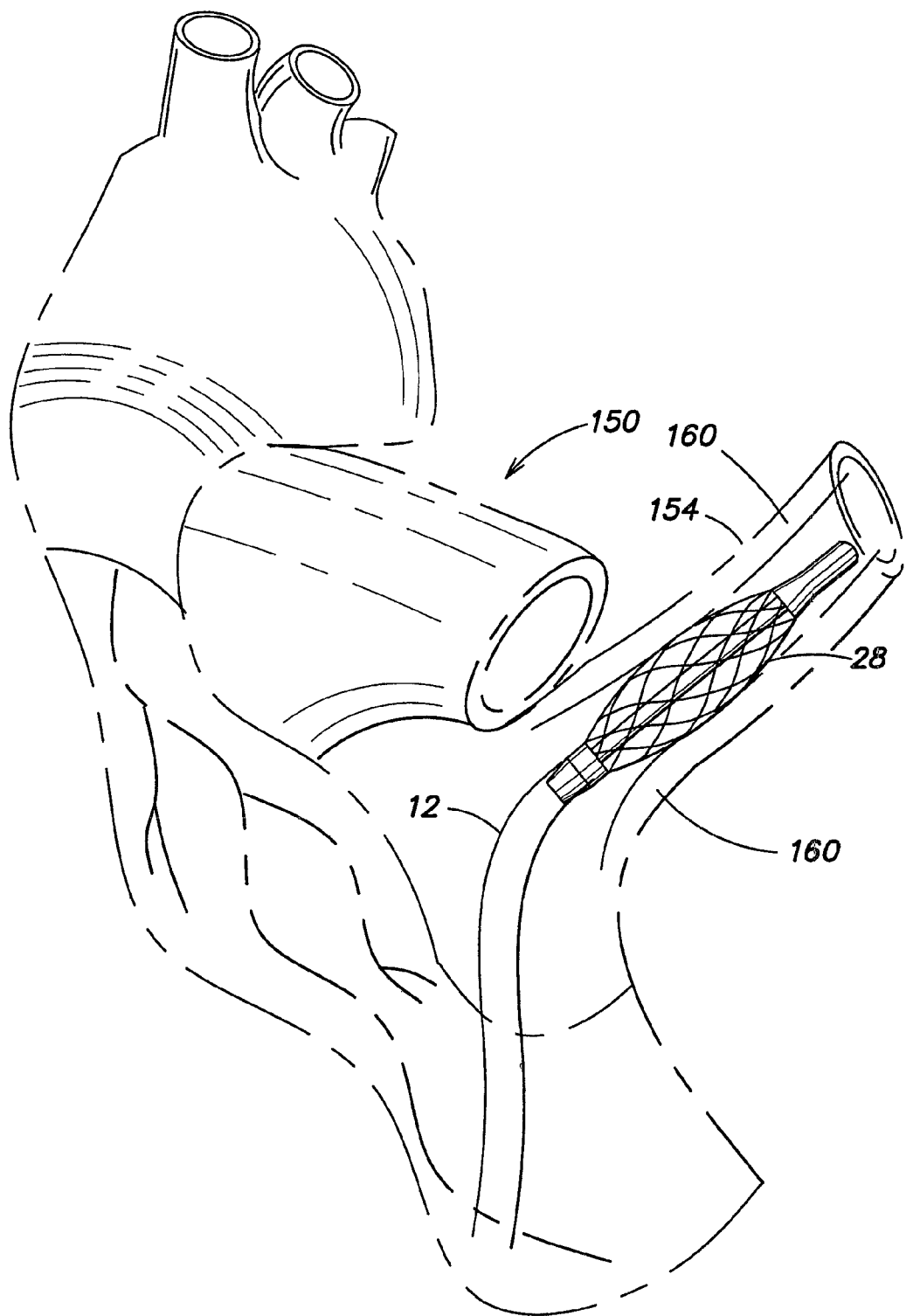

Reference is now made to FIGS. 22, 23, and 24, which figures illustrate how the catheter of the present invention may be used in endocardial and epicardial applications.

Referring to FIG. 22, this figure illustrates an endocardial ablation procedure. In this procedure, catheter shaft 12 is introduced into a patient's heart 150. Appropriate imaging guidance (direct visual assessment, camera port, fluoroscopy, echocardiographic, magnetic resonance, etc.) can be used. FIG. 22 in particular illustrates catheter shaft 12 being placed in the left atrium of the patient's heart. Once catheter shaft 12 reaches the patient's left atrium, it may then be introduced through an ostium 152 of a pulmonary vein 154. As illustrated, braided conductive member 28 is then expanded to its deployed position, where, in the illustrated embodiment, braided conductive member 28 forms a disk. Catheter shaft 12 then advanced further into pulmonary vein 154 until the distal side 156 of braided conductive member 28 makes contact with the ostium of pulmonary vein 154. External pressure may be applied along catheter shaft 12 to achieve the desired level of contact of braided conductive member 28 with the ostium tissue. Energy is then applied to the ostium tissue 152 in contact with braided conductive member 28 to create an annular lesion at or near the ostium. The energy used may be RF (radiofrequency), DC, microwave, ultrasonic, cryothermal, optical, etc.

Reference is now made to FIG. 23, which figure illustrates an epicardial ablation procedure. As illustrated in FIG. 23, catheter shaft 12 is introduced into a patient's thoracic cavity and directed to pulmonary vein 154. Catheter 10 may be introduced through a trocar port or intraoperatively during open chest surgery Using a steering mechanism, preformed shape, or other means by which to make contact between braided conductive member 128 and the outer surface 158 of pulmonary vein 154, braided conductive member 28 is brought into contact with the outer surface 158 of pulmonary vein 154. Appropriate imaging guidance (direct visual assessment, camera port, fluoroscopy, echocardiographic, magnetic resonance, etc.) can be used. As illustrated in FIG. 23, in this procedure, braided conductive member 28 remains in its undeployed or unexpanded condition. External pressure may be applied to achieve contact between braided conductive member 28 with pulmonary vein 154. Once the desired contact with the outer surface 158 of pulmonary vein 154 is attained, ablation energy is applied to surface 158 via braided conductive member 28 using, for example, RF, DC, ultrasound, microwave, cryothermal, or optical energy. Thereafter, braided conductive member 28 may be moved around the circumference of pulmonary vein 154, and the ablation procedure repeated. This procedure may be used to create, for example, an annular lesion at or near the ostium.

Use of the illustrated endocardial or epicardial procedures may be easier and faster than using a single "point" electrode since a complete annular lesion may be created in one application of RF energy.

Reference is now made to FIG. 24 which figure illustrates an endocardial mapping procedure. In the procedure illustrated in FIG. 24, catheter shaft 12 is introduced into pulmonary vein 154 in the manner described in connection with FIG. 22. Once braided conductive 28 has reached a desired location within pulmonary vein 154, braided conductive member 28 is expanded as described in connection with, for example, FIGS. 2-5 until filaments 34 contact the inner wall 160 of pulmonary vein 154. Thereafter, electrical activity within pulmonary vein 154 may be detected, measured, and recorded by an external device connected to the filaments 34 of braided conductive member 28.

Access to the patient's heart can be accomplished via percutaneous, vascular, surgical (e.g. open-chest surgery), or transthoracic approaches for either endocardial or epicardial mapping and/or mapping and ablation procedures.

The present invention is thus able to provide an electrophysiology catheter capable of mapping and/or mapping and ablation operations. In addition, the catheter of the invention may be used to provide high density maps of a tissue region because electrocardiograms may be obtained from individual filaments 34 in braided conductive member 28 in either a bipolar or unipolar mode.

Furthermore, the shape of the electrode region can be adjusted by controlling the radial expansion of braided conductive member 28 so as to improve conformity with the patient's tissue or to provide a desired mapping or ablation profile. Alternatively, braided conductive member 28 may be fabricated of a material of sufficient flexural strength so that the tissue is preferentially conformed to match the expanded or partially expanded shape of the braided conductive member 28.

The catheter of the present invention may be used for mapping procedures, ablation procedures, and temperature measurement and control on the distal and/or proximal facing sides of braided conductive member 28 in its fully expanded positions as illustrated in, for example, FIG. 1. In addition, the catheter of the present invention can be used to perform "radial" mapping procedures, ablation procedures, and temperature measurement and control. That is, the outer circumferential edge 76, illustrated, for example, in FIG. 8, can be applied against an inner circumferential surface of a blood vessel.

Furthermore, being able to use the same catheter for both mapping and ablation procedures has the potential to reduce procedure time and reduce X-ray exposure.

The ability to expand braided conductive member 28 in an artery or vein against a tissue structure such as a freewall or ostium can provide good contact pressure for multiple electrodes and can provide an anatomical anchor for stability. Temperature sensors can be positioned definitively against the endocardium to provide good thermal conduction to the tissue. Lesions can be selectively produced at various sections around the circumference of braided conductive member 28 without having to reposition catheter 10. This can provide more accurate lesion placement within the artery or vein.

Braided conductive member 28, in its radially expanded position as illustrated in particular in FIGS. 1 and 8 is advantageous because, in these embodiments, it does not block the blood vessel during a mapping or ablation procedure, but allows blood flow through the braided conductive member thus allowing for longer mapping and/or ablation times, which can potentially improve accuracy of mapping and efficacy of lesion creation.

Having thus described at least one illustrative embodiment of the invention, various alterations, modifications, and improvements will readily occur to those skilled in the art.

Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A method for treating a condition of a patient, comprising acts of:
    introducing a portion of a catheter into a patient, the catheter having a braided conductive member at a distal end thereof;
    contacting an exterior wall surface of a blood vessel of a vasculature of the patient with the braided conductive member; and
    applying energy to the exterior wall surface via the braided conductive member with the distal end of the catheter including the braided conductive member positioned exterior of the vasculature of the patient to treat the condition.

2. The method of claim 1, wherein the braided conductive member is expandable from an undeployed position to a deployed position.

3. The method of claim 2, wherein, during the act of applying energy to the exterior wall surface, the braided conductive member is in the undeployed position.

4. The method of claim 1, wherein the blood vessel is the pulmonary vein.

5. The method of claim 4, wherein the act of applying energy to the exterior wall comprises applying the energy near an ostium of a pulmonary vein.

6. The method of claim 1, wherein the act of applying energy comprises forming at least one lesion on the exterior wall surface.

7. The method of claim 6, wherein the at least one lesion is annular.

8. The method of claim 1, wherein the catheter is steerable.

9. The method of claim 1, wherein the braided conductive member is partially insulated.

10. The method of claim 1, wherein the act of applying energy alters a property relating to the heart.

11. The method of claim 1, wherein the act of applying energy treats a cardiovascular condition.

12. The method of claim 1, wherein, during the act of applying energy, at least one sector of the braided conductive member is unenergized.

* * * * *